United States Patent
Walele et al.

(10) Patent No.: US 6,635,775 B1
(45) Date of Patent: Oct. 21, 2003

(54) REDUCED ODOR ESTERS AND PROCESS FOR PRODUCING SAME

(75) Inventors: Ismail Walele, Saddle Brook, NJ (US); Samad A. Syed, Paramus, NJ (US)

(73) Assignee: Finetex, Inc., Elmwood Park, NJ (US)

( * ) Notice: Subject to any disclaimer, the term of this patent is extended or adjusted under 35 U.S.C. 154(b) by 0 days.

(21) Appl. No.: 09/498,565

(22) Filed: Feb. 4, 2000

Related U.S. Application Data

(60) Provisional application No. 60/118,977, filed on Feb. 8, 1999.

(51) Int. Cl.$^7$ .................. C07C 51/42; C07C 53/00; C07C 69/76; C07C 67/48
(52) U.S. Cl. .............. 554/175; 554/176; 554/182; 554/227; 560/103; 560/112; 560/248
(58) Field of Search ............... 560/103, 112, 560/248; 554/175, 176, 182, 227

(56) References Cited

U.S. PATENT DOCUMENTS

| | | |
|---|---|---|
| 2,997,494 A | 8/1961 | Brown |
| 3,843,719 A | 10/1974 | Brady |
| 4,275,222 A * | 6/1981 | Scala, Jr. |
| 4,304,925 A | 12/1981 | Watanabe et al. |
| 4,322,545 A | 3/1982 | Scala, Jr. |
| 4,323,693 A | 4/1982 | Scala, Jr. |
| 4,323,694 A | 4/1982 | Scala, Jr. |
| 4,506,091 A | 3/1985 | Deardorff |
| 4,791,097 A | 12/1988 | Walele et al. |
| 5,270,461 A | 12/1993 | Walele et al. |
| 5,271,930 A | 12/1993 | Walele et al. |
| 5,302,746 A | 4/1994 | Koono et al. |
| 5,693,316 A | 12/1997 | Pereira et al. |
| 5,783,173 A | 7/1998 | Bonda et al. |

FOREIGN PATENT DOCUMENTS

| | | | |
|---|---|---|---|
| DE | 62047 | * | 6/1968 |
| WO | WO 88/06878 A1 | * | 9/1988 |

OTHER PUBLICATIONS

Hauser et al, Journal of the American Chemical Society, 1956, The Alkylation of Tertiary Esters of Dialkylacetic acids by Means of Alkali Amides. Synthesis of Trialkylacetic Acids, 78, pp. 3837–3841.*

Yoshino et al, Synthetic studies with carbonates. Part 6. Syntheses of 2-Hydroxyethyl Derivatives by Reactions of Ethylene Carbonate with Carboxylic Acids of Heterocycles, 1977, Journal of the Chemical Society, Perkin I, (11), pp. 1266–1272.*

* cited by examiner

Primary Examiner—Samuel Barts
Assistant Examiner—Paul A. Zucker
(74) Attorney, Agent, or Firm—Weingram & Associates, P.C.

(57) ABSTRACT

An improved process for preparing reduced-odor or odorless esters, preferably benzoate esters, octanoate esters, aliphatic emollient esters and glycol dibenzoate esters. The improved process comprises, in part, removing the esterification catalyst from the crude ester after the esterification reaction is substantially complete, before neutralization of acidity. The resultant ester compositions are odorless or have substantially reduced odor as compared to commercially available esters.

43 Claims, No Drawings

REDUCED ODOR ESTERS AND PROCESS FOR PRODUCING SAME

This application claims benefit of U.S. Ser. No. 60/118,977 filed Feb. 8, 1999.

BACKGROUND OF THE INVENTION

1. Field of the Invention

The present invention relates to reduced odor or odor-free esters, and more particularly to odor-free C12–C15 alkyl benzoate esters, octanoate esters, glycol dibenzoate esters, and other emollient esters, their process of manufacture and their use in cosmetics and personal care products as carriers or vehicles, or a diluents, solvents, plasticizers, emollients and solubilizers.

2. Description of the Related Art

Esters are known for a variety of different applications for cosmetic, pharmaceutical and medicinal purposes.

Numerous references describe the production and use of benzoic acid esters. None of these references teach or suggest the specific novel reduced odor or odorless benozate esters of this invention or the use of these and other reduced odor benzoate esters in cosmetics and personal care products.

For example, benzoate esters of certain alcohols and alcohol mixtures and their uses are disclosed in assignee's U.S. Pat. Nos. 4,323,694; 4,322,545; and 4,275,222, all to Scala; and U.S. Pat. Nos. 4,791,097; 5,270,461; and 5,271,930, all to Walele et al. The disclosures of these patents are incorporated herein by reference.

U.S. Pat. Nos. 4,323,694; 4,322,545; and 4,275,222 to Scala disclose benzoic acid esters and processes for making same, using methane sulfonic acid as a catalyst at temperatures of about 160° C. to 175° C. The catalyst containing crude ester is washed and dried. Although there is no specific teaching of such washings in Scala, the industry practice is to neutralize any residual acidity with an alkali water wash. The ester is then further washed, as necessary, and dried. The Scala patents do not disclose using stannous oxalate as a catalyst, running the reaction at very high temperatures (220° C. or more), or removal of the catalyst as a process improvement to improve the odor of the resultant esters.

U.S. Pat. Nos. 4,791,097; 5,270,461; and 5,271,930 to Walele et al. disclose benzoic acid esters and processes for making same. The processes disclose reacting benzoic acid with an alcohol, using a catalyst, heating and then cooling, and collecting distillate. The mixture was subsequently treated with, among other things, hydrogen peroxide, and heated at 80° C.–100° C. The ester component was collected, washed with neutralization, and then refined by washing and drying.

U.S. Pat. No. 2,997,494 to Brown discloses a method of preparing vinyl esters of carboxylic acids.

U.S. Pat. No. 3,843,719 to Brady discloses a process for preparing esters of carboxylic acids.

U.S. Pat. No. 4,304,925 to Watanabe et al. discloses a process for obtaining esters by reacting an organic carboxylic acid or its anhydride with an alcohol in the presence of an organometallic compound as a catalyst. There is no recognition of steps taken specifically to improve the odor of the esters.

U.S. Pat. No. 4,506,091 to Deardorff discloses a method for refining esters without the necessity of washing procedures. Improvement of the odor of the ester is not contemplated or recognized.

U.S. Pat. No. 5,302,746 to Koono et al. discloses a process for producing a carboxylic acid ester, using a countercurrently contacting column for neutralization.

U.S. Pat. No. 5,693,316 to Pereira et al. discloses fatty alkoxylate esters of aliphatic and aromatic dicarboxylic acids.

U.S. Pat. No. 5,783,173 to Bonda et al. discloses a sun-screen composition containing a UV-B dibenzoylmethane derivative such as PARSOL 1789, and a stabilizer/solubilizer for the dibenzoylmethane derivative, and mixtures thereof.

However, among the foregoing patents, none have the unique properties of the ester compositions described and claimed herein. None disclose or suggest a process for the production of esters and emollient esters which are odorless or which have extremely low odor due to the absence of odor-causing species such as aldehydes, carbonyl compounds, and the like. This is a vital property in numerous applications, as the esters may be incorporated into personal care products, where absence of odor is critical to consumer acceptance.

This is due in part to the failure of prior processes to recognize that removal of the catalyst improves the odor, and to the use of certain unsuitable catalysts. For instance, the Scala patents referred to above use Methane Sulfonic Acid (MSA) as a catalyst. The problem with using MSA as a catalyst is that it is soluble in the organic reactants. MSA dissolves in the organic matter during reaction and cannot be physically removed by filtration from the reaction mix. It is not heterogeneous as is the case with stannous oxalate and metal oxides. However, it is neutralized in the neutralization/washings which follow subsequent to the esterification reaction. So even after neutralization and washing, odorous esters are formed because the intrinsic odor from the raw materials remains. Another problem with MSA is that the reaction cannot be run at high temperatures; exceeding temperatures of about 170° C. to 175° C. results in formation of chocolate-colored organic matter. It has been found by applicants that the darker the ester product, generally the worse the odor. Esters made using MSA as a catalyst have been found by applicants to be odorous.

In developing formulations for personal care products, it is critical to utilize a product that lacks odor. Many emollients have a characteristic obnoxious odor that is difficult to mask. Masking odors is an inordinately difficult and expensive task. Known methods of producing esters and ester-emollients result in esters which are odorous, i.e., they have an MFL, a minimum fragrance level. This is a disadvantage because perfumes must then be added to mask or overcome the MFL. Additionally and/or alternatively, the esters are deodorized by various methods including filtering, bleaching clays, or steam distilling the esters. Masking the obnoxious odors of many emollients is both difficult and expensive.

The disadvantages of the known methods of producing esters and emollient esters are overcome by the process of the present invention. Unexpectedly, the esters of the invention are odorless or have a very small MFL, avoiding the need for perfumes and deodorization.

OBJECTS AND SUMMARY OF THE INVENTION

It is an object of the present invention to provide a process or producing esters and emollient esters which have a low odor, or MFL, or which are odorless, due to the absence of odor causing species such as aldehydes, carbonyl compounds, and the like.

It is another object of the invention to provide a process for making reduced odor or odorless esters and emollient esters for use in cosmetics and personal care products.

It is yet another object of the invention to provide a process for making reduced odor or odorless esters and emollient esters for use in products where the addition of perfumes is objectionable.

It is a further object of the invention to provide a process for making esters and emollient-esters for use in cosmetics and personal care products which reduces the need for perfumes in cosmetics and personal care products.

Yet another object of the invention is to provide a method for producing esters and emollient esters which obviate the need for extraneous filtration or deodorizing techniques to remove odor.

Another object of the invention is to provide a method of producing reduced odor or odorless cosmetics or personal care products using certain specific benzoic acid esters.

It is another object of the invention to provide low-odor or non-odorous esters and emollient esters by reducing or substantially eliminating odor causing species.

Yet another object of the invention is to provide novel esters which may serve as emollient's and which may also modify the odor characteristics of the products in which they are used.

It is another object of the invention to provide reduced odor or non-odorous esters and ester emollients for use in products where the use of perfumes is objectionable.

It is another object of the invention to provide reduced odor or non-odorous esters and ester emollients for use in cosmetics and personal care products to reduce the use of perfumes in these products.

Yet another object of the invention is to provide esters and ester emollients for use in products where the odor of the ester may interfere with that of other ingredients.

These and other objects are accomplished by providing an improved process for preparing reduced-odor or odorless esters, preferably benzoate esters, octanoate esters, aliphatic emollient esters and glycol dibenzoate esters. The improved process comprises, in part, removing the esterification catalyst from the crude ester after the esterification reaction is substantially complete, before neutralization of acidity. The resultant ester compositions are odorless or have substantially reduced odor as compared to commercially available esters.

DESCRIPTION OF THE INVENTION

The novel esters of this invention have unique properties in that they have reduced odor or are substantially odor-free. This property makes the compositions useful as a vehicle or carrier, emollient or solubilizer for toiletry and cosmetic formulations and personal care products, such as hair creams, hand cleaners, bath oils, suntan oils, anti-perspirants, perfumes, colognes, cold creams, electric pre-shaves, eye and throat oils, finger nail polish, topical pharmaceutical ointments, lipsticks, stick rouge, skin lotions and creams, skin moisturizers, cleansing creams, and after-bath splash and lotions, as well as other formulations. The foregoing list is only exemplary of the type of compositions in which the esters of this invention may be used, and, as such, is not to be considered limiting.

DETAILED DESCRIPTION OF THE INVENTION

The odor-free emollient esters produced by the process of the invention include:
a. Benzoate Esters in general, and C12–15 Alkyl Benzoate Esters in particular, as set forth in Example Nos. 1 through 11 below;
b. Octanoate Esters, and in particular, aliphatic cetearyl octanoate esters, as set forth in Example Nos. 12, 13, and 27 below.
c. Aliphatic.emollient esters, specifically, C12–15 Alkyl Octanoate Esters, as set forth in Example Nos. 14, 15, 25 and 26, below;
d. Glycol Dibenzoate esters, specifically Dipropylene Glycol Dibenzoate, as set forth in Example Nos. 16 and 17, below.

The preferred alcohol precursors used in preparing the odor-free benzoic acid esters of the invention are selected from the group consisting of alcohols containing from 3 to 22 carbon atoms, and preferably C12–C15 alcohols. Typical examples include octyl alcohol, lauryl alcohol, myristyl alcohol, cetyl alcohol, behenyl alcohol, oleyl alcohol, isostearyl alcohol, arachidyl alcohol, etc. The preferred alcohol is Neodol 25 (Shell Chemical Company).

The odor-free octanoate esters of the invention are obtained by reacting ethylhexanoic acid with an alcohol in accordance with the process of the invention. The alcohol is selected from the group consisting of alcohols containing from 3 to 22 carbon atoms, and preferably C12–C15 alcohols. Typical examples include octyl alcohol, lauryl alcohol, myristyl alcohol, cetyl alcohol, behenyl alcohol, oleyl alcohol, isostearyl alcohol, arachidyl alcohol, etc. The preferred alcohol is Neodol 25 from Shell Chemical Company.

The odorless aliphatic emollient esters of the invention are made by reaction of alcohols and carboxylic acids in accordance with the process of the invention. The alcohols may be alcohols such as those comprising 3 to 22 carbon atoms, e.g., octyl alcohol, decyl alcohol, lauryl alcohol, myristyl alcohol, cetyl alcohol, stearyl alcohol, oleyl alcohol, arachidyl alcohol, behenyl alcohol, isostearyl alcohol, etc. Preferably, the alcohol is a C12–C15 alcohol. Most preferably, the alcohol is Neodol 25 from Shell Chemical Co. The carboxylic acids may be selected from the group of carboxylic acids consisting of linear or branched, with 4 to 22 carbon atoms, such as octanoic acid, decanoic acid, ethylhexanoic acid, lauric acid, myristicacid, palmitic acid, stearic acid, oleic acid, behenic acid, isostearic acid and arachidic acid.

The odor-free glycol dibenzoate esters of the invention are prepared by reacting a glycol with benzoic acid in accordance with the process of the invention. The glycol comprises from 3 to 12 carbon atoms, preferably 6 to 12 carbon atoms. Most preferably, the glycol is dipropylene glycol.

The foregoing list is only exemplary of the type of precursors on which the emollient esters may be based, and, as such, is not to be considered limiting.

In a specific embodiment, and by way of illustration, this invention contemplates the production of low odor or odorless emollient-esters in accordance with the following equation:
A. Octanoate Ester Chemistry
FINESTER CST-8, also known as cetearyl octanoate, is a branched chain emollient ester; FINESTER EH-25 is an octanoate ester of C12–15 alcohol.

In the following discussion, FINESTER CST-8, FINESTER EH-35, FINSOLV PG-22, and FINSOLV TN are registered trademarks of Finetex, Inc., Elmwood Park, N.J., 07407.

Reacting 2-Ethyl Hexanoic Acid+C16–18 Alcohol (may be Cetyl or Stearyl Alcohol) in the presence of a catalyst produces Cetyl/Stearyl/Ethyl Hexanoate (also known as Cetyl/Stearyl Octanoate).

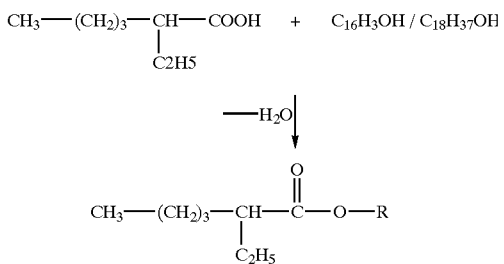

Where R=$C_{16}$–$C_{18}$ Alkyl (sold as FINESTER CST-8)

Reacting 2-Ethyl Hexanoic Acid+C12–15 Alkyl Alcohol in the presence of a catalyst produces C12–15 Alkyl Ethyl Hexanoate (also known as C12–15 Alkyl Octanoate), as follows:

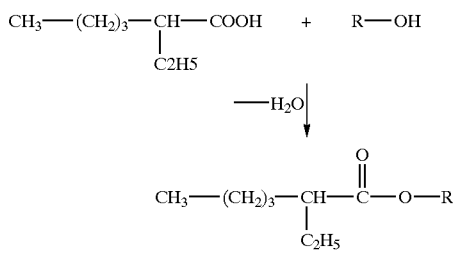

Where R=C12–15 Alkyl (Sold as FINESTER EH-25)

The odor-free, emollient benzoate esters of this invention are produced by reacting benzoic acid with an alcohol, as is known in the art, and as taught in the Scala and Walele et al. patents, supra. A catalyst is present during the reaction. The process for preparing the esters is preferably a batch process, but may also be a continuous process, for instance, conducted in a continuous extractor.

Superior, reduced odor or odorless esters are produced in part by removing the catalyst from the mass after the reaction is complete and before neutralization. The catalyst is preferably removed by filtration so that the crude ester mass is free of the catalyst particulate matter. Thereafter, the crude ester is worked up by neutralizing, washing and drying. The resultant processed refined ester is odorless or practically odorless as compared to prior art esters.

Applicants have discovered that removal of the catalyst from the mass after the reaction is complete and before neutralization has multiple benefits. These include reducing the use of alkalis for neutralization of organic acidity, thus reducing the formation of oxalic acid neutral species. Another benefit is reducing loss during the washing procedure by way of reducing the amount of inseparable emulsion phase (interphase) which causes loss of product, thus improving the yield. Removing the catalyst before neutralizing and washing the crude ester improves the yield and odor of the resultant ester and results in a sharp separation during the washing.

Thus, applicants have found that removal of the catalyst advantageously prevents the occurrence of undesirable side reactions which may interfere with formation of the desired esters. In the case of stannous oxalate as the catalyst, these undesirable side reactions include effects of alkalis on alcohol or ester, in the presence of stannous oxalate; the reaction of stannous oxalate with hydrogen peroxide to form oxalic acid; and oxidation of unreacted alcohol to aldehyde and ketone in the presence of hydrogen peroxide and stannous oxalate.

Another factor in reducing odor is the use of sodium borohydride for the treatment of the alcohol., i.e., C12–15 alcohol, before reacting with Benzoic Acid and before contacting the mixture of reactants and catalyst, to convert aldehyde and other species in the reaction to alcohol. Use levels of sodium borohydride can be from 10 ppm to 500 ppm.

Other starting alcohols or glycols (besides C12–15 alcohols), such as dipropylene glycol or C16–C18 alcohol, may be pretreated with sodium borohydride, but it is not a requirement of the process of the invention to do so. As shown in Example No. 1 below, Neodol 25 (Shell Chemical Company) is not pretreated with Sodium Borohydride, yet good odor results were obtained even without pretreatment. This is thought to be due to the fact that in this Example where the catalyst was removed, and hydrogen peroxide was not used in any step during the reaction and washing, there is such a minute amount of impurities in the form of aldehydes and ketones that, even without using sodium borohydride, the odor is very good. While the color of the ester is slightly higher, it is still good (less than 20 APHA).

In contrast, as can be seen from Example #2 below, when the starting alcohol was not pretreated with sodium borohydride, and the catalyst was not removed, and hydrogen peroxide was added to the crude ester before the washing step, the resulting ester had a mild to strong odor, there was a loss of yield in the form of increased interphase, but the resulting ester had very good color.

As demonstrated in Example #4 below, where the alcohol is pretreated with sodium borohydride, the catalyst is removed from the reaction mass, and hydrogen peroxide is added before neutralization of acidity, the resulting ester has a mild odor, there is loss of some yield, and the ester has a good color.

In summary, esters with the best odor and yield are obtained is where there is no pre-treatment with sodium borohydride, the catalyst is removed, and hydrogen peroxide is not added, as demonstrated in Example #1. Esters having adequate, but not as good, odor and yield, are obtained where there is no pre-treatment with sodium borohydride, the catalyst is removed, and hydrogen peroxide is added before neutralization in aqueous form, as demonstrated in Example #4. Esters having the worst odor and yield were obtained when there was no pretreatment with sodium borohydride, the catalyst was not filtered, and hydrogen peroxide was added to the anhydrous crude ester, as demonstrated in Examples #29 and #30 below. See Table III for comparative results.

The catalyst may be selected from the group consisting of stannous oxalate and metal oxides, such as zinc oxide. Stannous Oxalate is a catalyst in the category or group of Organometallics. It is also referred to as an organotin catalyst. Stannous Oxalate may be used in the range of 0.05% to 1.5% on the weight of the alcohols. Metal oxides in general, and zinc oxide in particular, may be used as catalysts in the range of 0.1% to 1.0% on the weight of the alcohols.

The preferred catalyst is Stannous Oxalate, which is insoluble in the reaction mixture, in the alcohol alone, or in the carboxylic acid alone. The advantage of using this catalyst is that it can be filtered or removed by other means from the crude ester. Methane sulfonic acid is not used as a catalyst because it cannot be physically removed by filtration or otherwise easily removed from the crude ester, unless it is washed.

The catalyst is removed from the crude ester after the reaction is complete and before neutralization. The reaction is deemed complete when the acid value is less than 10 mg KOH/g.

The reaction mixture may optionally be cooled to room temperature before removing the catalyst, preferably by filtration. Filtration may be accomplished by any conventional means, including using cartridges, filter strainers, filter press, or centrifuge. Thus, the products containing stannous oxalate and zinc oxide as catalysts are filtered to remove the heterogenous catalyst.

The next step is neutralization/washing of the optionally cooled crude ester which has been filtered. The crude ester with its acidity of no more than 10 mg KOH/g is neutral washed with stoichiometric, or slightly greater than stoichiometric, amounts of alkalis. This guarantees that acidity of the crude ester is overcome. This can optionally be verified by testing for acid value in the top layer of the mix. An acid value of 0 indicates that acidity has been completely neutralized. The alkalis can be sodium or potassium salts such as carbonates or hydroxides. The quantity of wash water can be from 1% to 25% on the weight of crude filtered ester. Sulfate salts or chloride salts of sodium or potassium are used at levels of 1% to 25% on the weight of total waters used for neutralization and/or washing. Thus, the optionally cooled but filtered crude ester is washed with neutralizing solutions containing an alkali metal carbonate to neutralize acidity of the catalyst and reactants, and sodium chloride or sodium sulfate. The sodium chloride or sodium sulfate salts are added for the purpose of phase separation of the two-phase systems of neutralizing/washing mixtures, i.e., the aqueous and organic phases. Phase separation is done at a temperature of 20° C. to 100° C., preferably between 40° C.–100° C., and more preferably between 60° C.–100° C.

After neutralization is complete, as evidenced by zero acidity and minor alkalinity, which assures acidity has been neutralized, then a certain quantity of hydrogen peroxide is added to the same first wash containing crude ester, water, sodium carbonate, and sodium sulfate, for the purpose of treating the ester, and especially for the purpose of bleaching the ester. If hydrogen peroxide is added before neutralization is complete, an odorous ester will result. The degree of odor depends on the stage of completion of neutralization. The more complete the neutralization of acidity, the better the odor of the resultant ester.

The concentration of hydrogen peroxide in its 30%–35% commercially available strength is in the range of 0.02% to 2.0% on the weight of the crude ester. This translates to a range of 6 ppm to 7000 ppm levels of hydrogen peroxide. Hydrogen peroxide is added to bleach the slight darkening in the reaction mixture.

The crude ester is in contact with hydrogen peroxide only in its abundantly wet form, i.e., only in the presence of large quantities of wash water or neutralization wash waters. Thus, if it is desired to bleach the reaction mixture with hydrogen peroxide, the treatment with hydrogen peroxide is done during the alkaline wash, but after the alkalines are entered and have neutralized the acidity, rather than in the anhydrous form of the crude ester. The use of hydrogen peroxide on the anhydrous crude ester at elevated temperature is believed to give or impart an odor to the composition which does not diminish subsequently, during the washing processes, as demonstrated by Ex. #29 below.

If the hydrogen peroxide is added simultaneously, i.e., in one step, with the neutralization or wash waters, as taught in the '097 and '461 Patents to Walele et al., supra, there is no improvement in the odor or color of the resultant ester. However, applicants have discovered that if the catalyst is removed, and hydrogen peroxide is added sequentially to the neutralization or wash waters, after neutralization is complete, esters having improved odor, color and yield are obtained.

In other words, it is not required in the invention process to add hydrogen peroxide. However, it is sometimes desirable to add hydrogen peroxide to improve (whiten) the color of the resulting ester. If it is desired to add hydrogen peroxide, it must be added after neutralization is complete, during the washing step, or after the washing step, while the ester is still wet, to eliminate or significantly reduce the odor of the resulting ester.

The process of the invention uses hydrogen peroxide in the aqueous washings (after neutralization is completed) to avoid contacting the anhydrous crude ester with hydrogen peroxide. Preventing hydrogen peroxide from contacting the anhydrous crude ester avoids the oxidation, if any, of the organic unreacted matter of the reaction mass. This prevents imparting an odor to the ester which cannot be washed out later.

Applicants have found that when hydrogen peroxide is added after neutralization of the acidity, the odor of the resulting ester is much improved, especially when the catalyst is removed. Applicants theorize this is because the chances of other side reactions occurring are negligible. For instance, the oxidation of alcohol to aldehydes, which typically creates odorous compounds, does not occur. This was not the case with prior art processes, such as that taught by U.S. Pat. No. 4,791,097 to Walele et al. In the '097 Patent, water, salt, sodium carbonate and hydrogen peroxide were added together simultaneously, without filtration of the catalyst, before neutralization of the acidity. The resultant ester has a strong odor, dark color, and poor yield, as shown in Example #31, below.

Applicants have found that odorous esters are formed when the anhydrous crude ester comes into contact with hydrogen peroxide at high temperatures of 80° C. to 100° C. in the presence of a catalyst, such as stannous oxalate.

It is preferred to have a second wash to remove alkalinity. The alkalinity is-removed easily by washing with water containing a salt, such as sodium sulfate or sodium chloride. The wet ester so obtained may also be subjected to a third wash of water and salt to insure no alkalinity remains. Then the wash water is removed.

The wet ester is contacted with hydrogen peroxide after neutralization is completed, in the same wash bath with the products of neutralization. Alternatively, hydrogen peroxide may be added separately, in a subsequent wash, after removal of the first wash water, following phase separation, while the ester is still wet and after neutralization is complete.

The next step is drying of the esters. The washed ester is subjected to drying at 100° C.–120° C. under reduced pressure of up to 1–5 mm Hg and until the residual moisture is less than 0.05%.

A final filtration step follows. The dry ester is filtered using diatomaceous earth filter aids.

Thus, applicants have found that removal of the catalyst before neutralization washing of the acidity with alkali, followed by drying of the ester, will result in odorless ester with some color. For exceptional color, hydrogen peroxide may be added to the filtered crude ester after neutralization of acidity and before drying in low pressure. There should not be any free hydrogen peroxide in the system. This will make possible the production of very low odor to odorless esters with good color.

Where the catalyst is not removed and hydrogen peroxide is added, the resultant ester has good color, but is odorous. Simply removing the catalyst and not adding hydrogen peroxide results in esters which are odorless and have some color. Removing the catalyst and adding hydrogen peroxide results in esters which are odorless and have good color, i.e., very low color.

Thus, the advantages provided by this invention are primarily production of an odorless ester, and improvement in the color and yield of the ester.

The benzoate esters of this invention may be used in skin care and personal care compositions. The amount used in skin care compositions is dependent on the type of skin care composition, the type and quantity of other ingredients, such as cosmetic ingredients used, and the amount and type of functional additives that are utilized. Typically, the amount of benzoate ester used ranges from about 0.5% to about 80%, by weight, of the skin care compositions. For example, a facial cream may only have about 0.5%, while a massage oil may have up to about 80% by weight.

Still higher amounts may be used in, for example, bath oils, e.g. 95%.

Further, the benzoate esters of this invention possess other unusual physio-chemical properties, which can make them suitable for use as emollient carriers in cosmetic formulations, and for use as solvents and emollient carriers in general cleaning compositions, such as in hand, face, and body creams and lotions. Thus, the benzoate esters described herein may serve not only as emollients and carriers, but may also exhibit one or more other functions.

The benzoic acid esters and emollient esters of the invention have properties in common with the C12–C15 benzoate and other esters of the prior art, such as the '545 Patent to Scala, in terms of being less greasy, less oily having low cloud point and pour points, low toxicity, ease of emulsification, high spreading coefficient, acid and alkaline stability, the ability to form gels with suspending agents, water solubility/dispersibility, and the ability to act as solvents for many common skin and hair care ingredients. This is because the process of the invention utilizes the same starting or raw materials as the '545 Patent to Scala, but uses a different process to produce the esters. The process of the invention results in the production of esters having improved odor and color, and greater yields, as compared to the esters of the '545 Patent to Scala. The improved yield is a further benefit of the process of the invention; by removing the catalyst there are less impurities to be washed, and no side reactions occurring during washing.

The following are non-limiting examples of processes for preparing the ester compositions of the invention and comparative examples of processes for preparing ester compositions of the prior art (Examples 1 to 31); uses of the compositions in specific cosmetic or personal care product formulations wherein the property of reduced or no fragrance is useful (Examples 32 to 35); and odor panel test results (Examples 36 to 37). In the Examples, as well as throughout this application, the chemical and scientific symbols have their customary meanings and all percents are weight percents unless otherwise specified.

Example Nos. 1 through 31 identify esters produced by the old process, and the new process of the invention. For ease of identification, each ester is identified by both an Example Number and a Reference No., where applicable. This identification system is used in the subsequent Tables III, III-A, III-B, III-C and III-D.

By "other process" in the Examples below, and the corresponding Tables, unless otherwise specified, is meant a process of the prior art as described, using FINESOLV TN® available from Finetex, Inc. as the raw material, wherein the catalyst is not removed during the reaction before neutralization and washing. Unless otherwise specified, it is not intended to refer to the exact process taught in the '545 Scala patent, as Scala teaches use of MSA as a catalyst, and the invention contemplates use of stannous oxalate or zinc oxide as the catalyst. Furthermore, Scala teaches reacting MSA at a lower temperature than the stannous oxalate catalyst is reacted at in the process of the invention. Color in the Examples below is measured using ASTM D-1209 on the APHA scale of the American Public Health Association. APHA scores less than 20 denote good color, with scores of 5 to 10 signifying superior color, i.e., clear color or absence of color. APHA scores over 20 are not good, as a yellow tint is visible, becoming progressively more colored as the APHA scores increase.

BENZOIC ACID ESTER COMPOSITIONS

EXAMPLE #1 (115-178)

Preparation of $C_{12-15}$ Alkyl Benzoate by New Process

In 1000 ml four neck round bottom flask equipped with glass stirrer, distillation head, condenser, thermometer and receiver, added 368.1 grams (1.805 moles) of Neodol 25 (Shell Chemical Company) and 225.54 grams (1.850 moles) of Benzoic Acid. The temperature was raised to 80° C. with good flow of nitrogen. At 80° C., added 0.84 grams of Stannous Oxalate and continued to heat to 200° C. maintaining a good flow of nitrogen over 1 hour. The reaction mixture was then raised to 240° C. in the next 2 hours and held for 1 hour over a vacuum of 28" Hg. The distillate (water of reaction) collected was 32 grams against theoretical estimates of 33.2 grams. The ester had the acidity of 3.4 mg KOH/g. The reaction mixture was cooled to 40° C. under nitrogen and filtered on Buckner Funnel with Whatman Paper #1 to remove any residual Stannous Oxalate. To the 400 grams filtered crude ester, added pre-dissolved 2.0 grams Sodium Chloride and 1.28 grams Sodium Carbonate in 64 grams water. Heated the mixture to 80° C. A sharp separation was observed upon standing for an hour with a small amount of interphase of approximately 3 grams. The wash procedure was repeated two more times with predissolved 1.28 grams Sodium Chloride in 64 grams of water. The washed aqueous ester was then. heated to 120° C. with a vacuum of 30" Hg to remove any residual 10 moisture and organic volatiles. When the moisture was <0.05%, cooled the mass to 40° C. under nitrogen and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 391 grams |
| % Yield: | 97.75 |
| Appearance: | Clear liquid |
| Acid Value: | 0.01 mg KOH/g |
| Water %: | 0.02 |
| Refractive Index: | 1.4850 |
| Color: | <15 APHA |
| Saponification Value: | 182 mg KOH/g |
| Odor: | Odorless |

Example #1 demonstrates production of a superior, odorless ester due merely to the removal of the catalyst, even without pretreatment of the alcohol with sodium borohydride, and even when no hydrogen peroxide was added. The color of the resultant ester is a slightly darker shade, but still within the very acceptable range for color, i.e., APHA less than 20.

EXAMPLE #2 (112-51)
(Preparation of $C_{12-15}$ Alkyl Benzoate by Other Process)

In 1000 ml four neck round bottom flask equipped with glass stirrer, distillation head, condenser, thermometer and receiver, added 368.1 grams (1.805 moles) of Neodol 25 (Shell Chemical Company) and 225.54 grams (1.850 moles) of Benzoic Acid. The temperature was raised to 80° C. with good flow of nitrogen. At 80° C. added 0.84 grams of Stannous Oxalate and continued to heat to 200° C. maintaining a good flow of nitrogen over 1 hour. The reaction mixture was then raised to 240° C. in the next 2 hours and held for 1 hour over a vacuum of 28" Hg. The distillate (water of reaction) collected was 32 grams against theoretical estimates of 33.2 grams. The ester had the acidity of 3.0 mg KOH/g. The reaction mixture was cooled to 100° C. and added 2 grams of 35% Hydrogen Peroxide. The resulting improved color ester was cooled to 40° C. To the 400 grams crude ester added pre-dissolved 2.0 grams Sodium Chloride and 1.28 grams Sodium Carbonate in 64 grams water. Heated the mixture to 80° C. Separation was observed upon standing for an hour with a big amount of Interphase of approximately 18 grams. The wash procedure was repeated two more times with predissolved 1.28 grams Sodium Chloride in 64 grams of water. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 380 grams |
| % Yield: | 95.00 |
| Appearance: | Clear liquid |
| Acid Value: | 0.01 mg KOH/g |
| Water %: | 0.03 |
| Refractive Index: | 1.4847 |
| Color: | <5 APHA |
| Saponification Value: | 181.5 mg KOH/g |
| Odor: | Mild to strong odor. Not an odorless product |

Example #2 is the same as Example #1, with the exception that the catalyst is not removed, and hydrogen peroxide is added to the anhydrous crude ester. The resulting odor has a mild to strong odor due to oxidation of the alcohol to aldehyde in the presence of peroxide and stannous oxalate.

EXAMPLE #3 (121-190)
(Preparation of C12–15 Alkyl Benzoate by Invention Process)

In 1000 ml four neck round bottom flask equipped with glass stirrer, distillation head, condenser, thermometer and receiver, added 372.0 grams (1.805 moles) of Neodol 25 (Shell Chemical Company) pretreated with Sodium Borohydride (500 ppm) and 228 grams (1.850 moles) Qf Benzoic Acid. The temperature was raised to 80° C. with good flow of nitrogen. At 80° C. added 0.84 grams of Stannous Oxalate and continued to heat to 200° C. maintaining a good flow of nitrogen over 1 hour. The reaction mixture was then raised to 240° C. in next 2 hours and held for 1 hour over a vacuum of 28" Hg. The distillate (water of reaction) collected was 32 grams against theoretical estimates of 33.2 grams. The ester had the acidity of 3.5 mg KOH/g. The reaction mixture was cooled to 40° C. and filtered on Buckner Funnel with Whatman Paper #42 to remove any residual Stannous Oxalate. To the 400 grams filtered crude ester added pre-dissolved 2.0 grams Sodium Chloride and 1.28 grams Sodium Carbonate in 64 grams water. Heated the mixture to 80° C. A sharp separation was observed upon standing for an hour with a small amount of interphase of approximately 2.5 grams. The wash procedure was repeated two more times with pre-dissolved 1.28 grams Sodium Chloride in 64 grams of water. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 385 grams |
| % Yield: | 96.25 |
| Appearance: | Clear liquid |
| Acid Value: | 0.008 mg KOH/g |
| Water %: | 0.01 |
| Refractive Index: | 1.4850 |
| Color: | <20 APHA |
| Saponification Value: | 180.22 mg KOH/g |
| Odor: | Practically odorless |

Example #3 demonstrates production of a practically odorless ester having good color, where the alcohol was pretreated with sodium borohydride, the catalyst was filtered out, and no hydrogen peroxide was added.

EXAMPLE #4 (112-141)
(Preparation of $C_{12-15}$ Alkyl Benzoate by Other Process)

In 1000 ml four neck round bottom flask equipped with glass stirrer, distillation head, condenser, thermometer and receiver, added 368.1 grams (1.805 moles) of Neodol 25 (Shell Chemical Company) pretreated with Sodium Borohydride and 225.54 grams (1.850 moles) of Benzoic Acid. The temperature was raised to 80° C. with good flow of nitrogen. At 80° C. added 0.84 grams of Stannous Oxalate and continued to heat to 200° C. maintaining a good flow of nitrogen over 1 hour. The reaction mixture was then raised to 240° C. in next 2 hours and held for 1 hour over a vacuum of 28" Hg. The distillate (water of reaction) collected was 31.2 grams against theoretical estimates of 33.2 grams. The ester had the acidity of 3.3 mg KOH/g. The reaction mixture was cooled to 100° C. and added 2 grams of 35% Hydrogen Peroxide. The resulting improved color ester was cooled to 40° C. To the 400 grams crude ester added pre-dissolved 2.0 grams Sodium Chloride and 1.30 grams Sodium Carbonate in 64 grams water. Heated the mixture to 80° C. Separation was observed upon standing for an hour with a reasonable amount of interphase of approximately 14 grams. The wash procedure repeated two more times with pre-dissolved 1.28 grams. Sodium Chloride in 64 grams of water. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 384 grams |
| % Yield: | 96.0 |
| Appearance: | Clear liquid |
| Acid Value: | 0.01 mg KOH/g |
| Water %: | 0.025 |
| Refractive Index: | 1.48450 |
| Color: | <5 APHA |
| Saponification Value: | 180.6 mg KOH/g |
| Odor: | Mild odor but not an odorless product |

EXAMPLE #5 CR (Preparation of $C_{12-15}$ Alkyl Benzoate by Invention Process)

A 10,000-lb. batch of FINSOLV TN was made in the plant on commercial scale by following the procedure of Example #3, including pretreatment with sodium borohydride. One gallon of sample was withdrawn from the reactor after the reaction showed acidity <3.0 mg KOH/g. This anhydrous crude ester before Hydrogen Peroxide treatment and washing has haze in it, with light yellow color. Upon standing, the Stannous Oxalate settled in the bottom of the jar, but still the product was not crystal clear. Upon mixing and filtering through Buckner Funnel on Whatman Paper #4 the product became clear liquid. This crude ester was used in the following examples. Note that the liquid of;Ex. #5 CR is unfiltered. In some of the following examples, the liquid of Ex. 5 CR is subsequently filtered.

EXAMPLE #5 (115-172)

(Preparation of C12–15 Alkyl Benzoate by Invention Process)

To 600 grams of unfiltered crude ester of Example #5 CR added pre-dissolved 3.0 grams Sodium Chloride and 1.2 grams Sodium Carbonate in 96 grams water. Heated the mixture to 80° C. Separation was observed upon standing for an hour with interphase of approximately 53 grams. The wash procedure was repeated two more times with pre-dissolved 3.0 grams Sodium Chloride in 96 grams of water and in both cases separation was sharp, with approximately 2 to 3 grams of interphase found. The washed aqueous ester was then heated to 120° C. with a vacuum of 30" Hg to remove any residual moisture and organic volatiles. When the moisture was <0.05%, cooled the mass to 40° and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 560 grams |
| % Yield | 93.33 |
| Loss During Washing % : | 6.67 |
| Appearance: | Clear liquid |
| Acid Value: | 0.02 mg KOH/g |
| Water %: | 0.02 |
| Refractive Index: | 1.4850 |
| Color: | <20 APHA |
| Saponification Value: | 181.66 mg KOH/g |
| Odor: | Odorless |

It is noted that even without the addition of hydrogen peroxide, the ester is superior in odor and color.

EXAMPLE #6 (115-174)

(Preparation of C12–15 Alkyl Benzoate by Other Process)

To 600 grams unfiltered crude ester of Example #5 CR added pre-dissolved 3.0 grams Sodium Chloride and 1.2 grams Sodium Carbonate in 96 grams water. Heated the mixture to 80° C. and acidity of the mixture was <0.1 mg. Added 5.76 grams 35% Hydrogen Peroxide and mixed for an hour at 80° C. Separation was observed upon standing for an hour with interphase of approximately 36 grams. The wash procedure was repeated two more times with predissolved 3.0 grams Sodium Chloride in 96 grams of water and in both cases separation was not sharp, with interphase of approximately 31 and 17 grams was found. The washed aqueous ester was then heated to 120° C. with a vacuum of 30" Hg to remove any residual moisture and organic volatiles. When the moisture level was <0.05%, cooled the mass to 40° C. and added 0.1 grams of Diatomaceous Earth filter aids. Mixed the: refined ester for 30 minutes and filtered on Buckner Funnel with Whatman Paper #42.

The following physical and chemical properties were observed:

| | |
|---|---|
| Yield: | 550 grams |
| Yield % : | 91.66 |
| Loss During Washing % : | 8.33 |
| Appearance: | Clear liquid |
| Acid Value: | 0.03 mg KOH/g |
| Water %: | 0.01 |
| Refractive Index: | 1.48475 |
| Color: | <10 APHA |
| Saponification Value: | 180.92 mg KOH/g |
| Odor: | Strong Odor |

Example #6 is based on the plant-production batch of 10,000 lb. of Example #5CR, where a small amount of approximately one gallon was taken out and filtered in the lab for further study. Before filtration of the one gallon, 600 grams of crude, unfiltered ester was purified by adding hydrogen peroxide to the crude ester at 80° C. to 100° C., then washing with sodium carbonate and sodium sulfate in the presence of the catalyst. The effect of filtration of the catalyst vs. no filtration of the catalyst was compared.

The strong odor of the resulting ester may be explained by the addition of hydrogen peroxide at high temperatures to the anhydrous, unfiltered, crude ester. The stannous oxalate was present in the system to act as a catalyst for oxidation of alcohol to aldehyde when hydrogen peroxide, the source of nascent oxygen, was added.

EXAMPLE #7 (115-176)

(Preparation of $C_{12-15}$ Alkyl Benzoate by Invention Process)

To 600 grams crude ester of Example #5 CR (filtered on Buckner Funnel with Whatman paper #42 in the lab), added pre-dissolved 3.0 grams Sodium Chloride and 1.2 grams Sodium Carbonate in 96 grams water. Heated the mixture to 80° C. Separation was observed upon standing for an hour with interphase of approximately 42 grams. The wash procedure was repeated two more times with pre-dissolved 3.0 grams Sodium Chloride in 96 grams of water and in both cases separation was sharp with interphase of approximately 4 and 0 grams was found. The washed aqueous ester was then heated to 120° C. with a vacuum of 30" Hg to remove any residual moisture and organic volatiles. When the moisture level was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 570 grams |
| Yield % : | 95.00 |
| Loss During Washing % : | 5.0 |
| Appearance: | Clear liquid |
| Acid Value: | 0.01 mg KOH/g |
| Water %: | 0.01 |
| Refractive Index: | 1.4850 |
| Color: | <20 APHA |
| Saponification Value: | 182.10 mg KOH/g |
| Odor: | Practically odorless |

In Example #7, the crude ester was filtered to remove the catalyst. As hydrogen peroxide was not added at all, and there was no catalyst in the washing, there is no source of nascent oxygen for an oxidation reaction. Even though there is some free alcohol in the system, the formation of odorous material is practically zero. For this reason, the ester is practically odorless. The extremely low interphases explains the high yield, as interphase is the lost or waste material.

EXAMPLE #8 (118-76)

(Preparation of $C_{12-15}$ Alkyl Benzoate by Invention Process)

To the 340 gram crude ester of Example #5 CR (filtered in the lab on Buckner Funnel with Whatman paper #4.2 added pre-dissolved 8.8 grams Potassium Chloride and 0.5 grams Potassium Carbonate in 88.4 grams water and 1.7 grams 35% Hydrogen Peroxide. Heated the mixture to 80° C. Separation was observed upon standing for an hour with interphase 1.20 grams. The wash procedure was repeated two more times with pre-dissolved 8.8 grams Potassium Chloride in 88.4 grams water and in both cases separation was sharp with interphase of approximately 0.4 and 0.2 grams was found. The washed aqueous ester was then heated to 120° C. with a vacuum of 30" Hg to remove any residual moisture and organic volatiles. When the moisture level was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 320 grams |
| Yield % : | 94.41 |
| Loss During Washing % : | 5.59 |
| Appearance: | Clear liquid |
| Acid Value: | 0.025 mg KOH/g |
| Water %: | 0.02 |
| Refractive Index: | 1.48475 |
| Color: | <5 APHA |
| Saponification Value: | 180.50 mg KOH/g |
| Odor: | Mild Odor |

In Example #8, the alcohol was pretreated with sodium borohydride, the catalyst was filtered, and hydrogen peroxide was added with the neutralization/wash waters, before neutralization of acidity. Salts are used in the second and third washes. The resultant ester has a mild odor.

EXAMPLE #9 (118-78)

(Preparation of $C_{12-15}$ Alkyl Benzoate by Invention Process)

To the 340 gram crude ester of Example #5 CR (filtered in the lab on Buckner Funnel with Whatman paper #42 added pre-dissolved 8.8 grams Potassium chloride and 1.0 grams Potassium Carbonate in 88.4 grams water and 1.7 grams 35% Hydrogen Peroxide. Heated the mixture to 80° C. Separation was observed upon standing for an hour with interphase 13.3 grams. The wash procedure was repeated two more times without Potassium Chloride in 88.4 grams of water and in both cases separation was sharp with no interphase was observed. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 335 grams |
| Yield % : | 98.53 |
| Loss During Washing % : | 1.47 |
| Appearance: | Clear liquid |
| Acid Value: | 0.01 mg KOH/g |
| Water %: | 0.015 |
| Refractive Index: | 1.48475 |
| Color: | <5 APHA |
| Saponification Value: | 180.70 mg KOH/g |
| Odor: | Mild Odor |

In Example #9, the same procedure as Example #8 is followed, except that potassium chloride and potassium carbonate salts are not added in the second and third washes. The resultant ester has a mild odor due to the addition of hydrogen peroxide into the system before neutralization of acidity. The yield is high.

EXAMPLE #10 (118-89)

(Preparation of $C_{12-15}$ Alkyl Benzoate by Invention Process)

To the 340 grams crude ester of Example #5 CR (filtered in the lab on Buckner Funnel with Whatman paper #42 added pre-dissolved 8.8 grams Potassium Chloride and 1.7 grams 35% Hydrogen Peroxide in 88.4 grams of water. Heated the mixture to 80° C. and when there was no free Hydrogen Peroxide in the mixture added 1.0 grams Potassium Carbonate and held for one hour at 80° C. Separation was observed upon standing for an hour with interphase 36 grams. The wash procedure was repeated two more times with pre-dissolved Potassium Chloride in 88.4 grams of water and in both cases separation was sharp with interphase of approximately 1 gram was observed. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 330 grams |
| Yield % : | 97.05 |

-continued

| | |
|---|---|
| Loss During Washing % : | 2.95 |
| Appearance: | Clear liquid |
| Acid Value: | 0.15 mg KOH/g |
| Water %: | 0.01 |
| Refractive Index: | 1.48475 |
| Color: | <5 APHA |
| Saponification Value: | 181.05 mg KOH/g |
| Odor: | Odorless |

In Example #10, odorless esters were obtained because the catalyst was filtered, hydrogen peroxide was consumed before addition of potassium carbonate, and the system was aqueous.

EXAMPLE #11 (118-92)
(Preparation of $C_{12-15}$ Alkyl Benzoate by Invention Process)

To the 340 grams crude ester of Example #5 CR (filtered in the lab on Buckner Funnel with Whatman paper #42 added 1.7 grams 35% Hydrogen Peroxide. Heated to 80° C. and mixed for 30 minutes. When there was no free Hydrogen Peroxide, added pre-dissolved 8.8 grams Potassium Chloride and 1.0 grams Potassium Carbonate in 88.4 grams of water. Mixed the mixture at 80° C. for another 30 minutes. Separation was observed upon standing for an hour with interphase of approximately 23 grams. The wash procedure was repeated two more times with predissolved 8.8 grams Potassium Chloride in 88.4 grams of water and in both cases separation wa.45 sharp with interphase of approximately 2 & 1 gram was found. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 325 grams |
| Yield % : | 95.58 |
| Loss During Washing % : | 4.42 |
| Appearance: | Clear liquid |
| Acid Value: | 0.01 mg KOH/g |
| Water %: | 0.015 |
| Refractive Index: | 1.4850 |
| Color: | <5 APHA |
| Saponification Value: | 180.75 mg KOH/g |
| Odor: | Mild Odor |

In Example 11, the alcohol was pretreated with sodium: borohydride, the catalyst was filtered, and hydrogen peroxide was added to the ester before the wash; this is not .an aqueous system. Some free benzoic acid and alcohol is present in the system. The chances of a reaction between the alcohol, hydrogen peroxide and benzoic acid are favored at that temperature for formation of odorous species. The resultant ester has a mild odor.

EXAMPLE #12 (115-169)
(Preparation of Cetearyl Octanoate by Other Process)

In 1000 ml four neck round bottom flask equipped with glass stirrer, distillation head, condenser, thermometer and receiver, added 411.58 grams (1.576 moles) of Cetearyl Alcohol and 238.42 grams (1.655 moles) of Ethylhexanoic Acid. The temperature was raised to 80° C. with good flow of nitrogen. At 80° C. added 1.95 grams of Stannous Oxalate and continued to heat to 200° C. maintaining a good flow of nitrogen over 1 hour. The reaction mixture was then raised to 220° C. in next one hour and held for 5 hours. The distillate (water of reaction) collected was 27.50 grams against theoretical estimates of 29.80 grams. The ester had the acidity of 5.61 mg KOH/g. The reaction mixture was cooled to 100° C. and added 4.0 grams 35% Hydrogen Peroxide. Mixed the reaction mass at 100° C. for an hour and then cooled to 40° C. To the 600 grams crude ester added predissolved 5.0 grams Sodium Carbonate and 7.2 grams Sodium Sulfate in 120 grams water. Heated the mixture to 80° C. Separation was observed upon standing for an hour with 37 grams of interphase was found. The wash procedure repeated two more times with pre-dissolved 7.2 grams Sodium Sulfate in 120 grams of water. In both cases approximately 6 grams of interphase was found upon standing. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 520 grams |
| Yield % : | 86.66 |
| Appearance: | Clear liquid |
| Acid Value: | 0.02 mg KOH/g |
| Water %: | 0.02 |
| Color: | <10 APHA |
| Saponification Value: | 140 mg KOH/g |
| Odor: | Strong Odor |

EXAMPLE #13 (118-245)
(Preparation of Cetearyl Octanoate by Process of Invention)

In 1000 ml four neck round bottom flask equipped with glass stirrer, distillation head, condenser, thermometer and receiver, added 381.24 grams (1.460 moles) of Cetearyl Alcohol and 216.90 grams (1.50 moles) of 2 Ethylhexanoic Acid. The temperature was raised to 80° C. with good flow of nitrogen. At 80° C. added 1.80 grams of Stannous Oxalate and continued to heat to 200° C. maintaining a good flow of nitrogen over one hour. The reaction mixture was then raised to 220° C. in next hour and held for five hours. The distillate (water of reaction) collected was 24.2 grams against theoretical estimates of 27.12 grams. The ester had the acidity of 3.3 mg KOH/g. The reaction mixture was cooled to 40° C. and filtered on Buckner Funnel with Whatman Paper #4 to remove any residual Stannous Oxalate. To 250 grams filtered crude ester was heated to 80° C. and added pre-dissolved 5.5 grams Sodium Sulfate in 55 grams water and 0.625 grams 35% Hydrogen Peroxide. Mixed the mixture for 30 minutes and when the amount of free Hydrogen Peroxide was 10 ppm added 1.325 grams of Sodium Carbonate. Mixed the mixture for 30 minutes and upon standing a good separation was observed. A minimal amount of interphase of approximately 10 grams was found. The wash procedure was repeated two more times with 5.5 grams Sodium Sulfate pre-dissolved in 55 grams water. In both cases, separation was excellent with less than 1 gram of interphase was found upon standing. The washed aqueous ester was then heated to 120° C. with a vacuum of 3.0" Hg to remove any residual moisture and organic volatiles. When the moisture was <0.05%, cooled the mass to 40° C. and added 0.1 grams of Diatomaceous Earth filter acids. Mixed the refined eater for 30 minutes and filtered on Buckner Funnel with Whatman Paper #42.

The following physical and chemical properties were observed:

| | |
|---|---|
| Yield: | 245 grams |
| Yield % : | 98.00 |
| Appearance: | Clear liquid |
| Acid Value: | 0.02 mg KOH/g |
| Color: | <20 APHA |
| Saponification Value: | 140 mg KOH/g |
| Odor: | Practically odorless |

EXAMPLE #14 (95-131)

(Preparation of $C_{12-15}$ Alkyl Octanoate by Other Process)

In 1000 ml four neck round bottom flask equipped with glass stirrer, distillation head, thermometer, condenser and receiver, added 346.32 grams (1.697 moles) of Neodol 25 (Shell Chemical Company) and 252.248 grams (1.751 moles) of 2 Ethylhexanoic Acid. The temperature was raised to 80° C. with good flow of nitrogen. At 80° C. added 1.20 grams of Stannous Oxalate and continued to heat to 200° C. maintaining a good flow of nitrogen over 1 hour. The reaction mixture was then raised to 220° C. in next hour and held for 3 hours. The distillate (water of reaction) collected was 28.8 grams against theoretical estimates of 31.55 grams. The ester had the acidity of 7.5 mg KOH/g. The reaction mixture was cooled to 100° C. and added 4.0 grams 35% Hydrogen Peroxide. Mixed the reaction mass at 100° C. for an hour and then cooled to 40° C. To the 500 grams crude ester added pre-dissolved 6 grams Sodium Sulfate and 3.0 grams Sodium Carbonate in 100 grams water. Heated the mixture to 80° C. Separation was observed upon standing for an hour with 40 grams of interphase was found. The wash procedure was repeated two more times with pre-dissolved 6.0 grams Sodium Sulfate in 100 grams water. In both cases approximately 8 grams of interphase was found upon standing. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 480 grams |
| Yield % : | 92.00 |
| Appearance: | Clear liquid |
| Color: | <10 APHA |
| Saponification Value: | 165 mg KOH/g |
| Odor: | Strong odor |

EXAMPLE #15 (118-221)

(Preparation of $C_{12-15}$ Alkyl Octanoate by Process of Invention)

In 3000 ml four neck round bottom flask equipped with glass stirrer, distillation head, condenser, thermometer and receiver, added 1038.96 grams (5.09 moles) of Neodol 25 (Shell Chemical Company) and 757.54 grams (5.26 moles), of 2-Ethylhexanoic Acid. The temperature was raised to 80° C. with good flow of nitrogen. At 80° C. added 3.6 grams of Stannous Oxalate and continued to heat to 200° C. maintaining a good flow of nitrogen over one hour. The reaction mixture was then raised to 220° C. in next hour and held for 3 hours. The distillate (water of reaction) collected was 90.62 grams against theoretical estimates of 94.68 grams. The ester had the acidity of 7.5 mg KOH/g. The reaction mixture was cooled to 40° C. and filtered on Buckner Funnel with Whatman Paper #4 to remove any residual Stannous Oxalate. To the 300 grams filtered crude ester added pre-dissolved 4.5 grams. Sodium Sulfate in 7.5 grams water and 1.25 grams 35% Hydrogen Peroxide. Mixed the mixture at 80° C. for 30 minutes and when the amount of free Hydrogen Peroxide was <10 ppm added 3.0 grams of Sodium Carbonate. Mixed the mixture for 30 minutes and upon standing a separation was observed with approximately 25 grams of interphase was found. The wash procedure was repeated two more times with 4.5 grams Sodium Sulfate pre-dissolved in 75 grams water. In both cases separation was excellent with less than 1 gram interphase found upon standing. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 270 grams |
| Yield % : | 96.66 |
| Appearance: | Clear liquid |
| Acid Value: | 0.02 mg KOH/g |
| Color: | <10 APHA |
| Saponification Value: | 165.8 mg KOH/g |
| Odor: | odorless |

EXAMPLE #16 (105-138)

(Preparation of DPG-Dibenzoate by Other Process)

In 500 ml four neck round bottom flask equipped with glass stirrer, distillation head, thermometer, condenser and receiver added 103.08 grams (0.77 moles) of Dipropylene Glycol and 196.92 grams (1.62 moles) of Benzoic Acid. The temperature was raised to 80° C. with good flow of nitrogen. At 80° C. added 0.6 grams of Stannous Oxalate and continued to heat to 200° C. maintaining a good flow of nitrogen over one hour. The reaction mixture was then raised to 220° C. in next hour and held for six hours. The distillate (water of reaction) collected was 56.5 grams against theoretical estimates of 58.10 grams. The ester had the acidity of 9.8 m KOH/g. The reaction mixture was cooled to 100° C. and added 1.5 grams 35% Hydrogen Peroxide. Mixed the reaction mass at 100° C. for an hour and then cooled to 40° C. To the 264 grams crude ester was added pre-dissolved 10 grams Sodium Chloride and 3.0 grams Sodium Carbonate in 50 grams water. Separation was observed upon standing for an hour with 10 grams of interphase found. The wash procedure was repeated two more times with predissolved 10 grams Sodium Chloride in 50 grams water. In both cases approximately 6 grams of interphase was found upon standing. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 220 grams |
| Yield % : | 83.33 |
| Appearance: | Clear liquid |
| Acid Value: | 0.11 mg KOH/g |
| Water % : | 0.02 |
| Color: | <10 APHA |
| Saponification Value: | 310.56 mg KOH/g |
| Odor: | strong odor |

EXAMPLE #17 (118-137)

(Preparation of DPG-Dibenzoate by Process of Invention)

In 1000 ml four neck round bottom flask equipped with glass stirrer, distillation head, condenser, thermometer and receiver, added 252.49 grams (1.88 moles) of Dipropylene Glycol and 442.40 grams (3.62 moles) of Benzoic Acid. The temperature was raised to 80° C. with good flow of nitrogen. At 80° C. added 3.36 grams of Stannous Oxalate and continued to heat to 200° C. maintaining a good flow of nitrogen over one hour. The reaction mixture was then raised to 220° C. in next hour and held for six hours. The distillate (water of reaction) collected was 120 grams against theoretical estimates of 130.55 grams. The ester had the acidity of 8.9 mg KOH/g. The reaction mixture was cooled to 40° C. and filtered on Buckner Funnel with Whatman Paper #4 to remove any residual Stannous Oxalate. To the 250 grams filtered crude ester added pre-dissolved 13.37 grams Sodium Chloride in 62.5 grams water and 1.25 grams 35% Hydrogen Peroxide. Mixed the mixture at 80° C. for 30 minutes and when the amount of free Hydrogen Peroxide was <10 ppm added 2.5 grams of Sodium Carbonate. Mixed the mixture for 30 minutes and upon standing a separation was observed with 5 grams of interphase found. The wash procedure was repeated two more times with 13.37 grams Sodium Chloride pre-dissolved in 62.5 grams water. In both cases separation was excellent with less than 1-gram interphase found upon standing. The washed aqueous ester was then heated to 120° C. with a vacuum of 30" Hg to remove any residual moisture and organic volatiles. When the mixture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 233 grams |
| Yield % : | 93.20 |
| Appearance: | Clear liquid |
| Acid Value: | 0.02 mg KOH/g |
| Color: | <10 APHA |
| Saponification Value: | 312.58 mg KOH/g |
| Odor: | odorless |

EXAMPLES #18, #19, #20, #21 (REF. Nos. 118-288-A; 118-288-B; 118-288-D; and 118-288-F, REPECTIVELY)

(C12–15 Alkyl Benzoate Esters of Other Process)

These preparations were of plant scale size of 10,000 lb. batches using the processes of Examples #2 and #4. These are based on other processes and were used for comparative purposes against the products of the invention processes.

EXAMPLES #22 and #22-C (118-288-A-NP and 118-288-C-NP)

($C_{12-15}$ Alkyl Benzoate Esters of Invention Process)

These preparations were large plant scale of 10,000-lb. size using the procedures of Examples #5 and #5CR. These are based on the invention processes.

EXAMPLES #23 and #24

(C12–15 Alkyl Octanoate Esters of Other Processes)

These preparations were of 10,000 lb. batch sizes using the other processes of Example #14.

EXAMPLE #25 (118-225)

(Preparation of $C_{12-15}$ Alkyl Octanoate by Process of Invention)

To the 300 grams filtered crude ester from Example #15 added pre-dissolved 4.5 grams Sodium Sulfate and 3.0 grams Sodium Carbonate in 75 grams water and 1.25 grams 35% Hydrogen Peroxide. Mixed the mixture for 30 minutes and upon standing a separation was observed with approximately 30 grams of Interphase. The wash procedure was repeated two more times with 4.5 grams Sodium Sulfate-predissolved in 75 grams water. In both cases separation was observed with less than 4 grams Interphase upon'standing. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 265 grams |
| Yield % : | 88.33 |
| Appearance: | Clear liquid |
| Acid Value: | 0.01 mg KOH/g |
| Water %: | 0.03 |
| Color: | <10 APHA |
| Saponification Value: | 165.8 mg KOH/g |
| Odor: | odorless |

EXAMPLE #26 (118-227)

(Preparation of $C_{12-15}$ Alkyl Octanoate by Process of Invention)

To the 300 grams filtered crude ester from Example #15 added pre-dissolved 4.5 grams Sodium Sulfate and 3.0 grams Sodium Carbonate in 75 grams water. Mixed the mixture for 30 minutes and upon standing a separation was observed with approximately 20 grams of Interphase. The wash procedure was repeated two more times with 4.5 grams Sodium Sulfate pre-dissolved in 75 grams water. In both cases separation was observed with less than 2 grams Interphase upon standing. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 275 grams |
| Yield % : | 91.66 |
| Appearance: | Clear liquid |
| Acid Value: | 0.02 mg KOH/g |
| Water %: | 0.03 |
| Color: | <20 APHA |
| Saponification Value: | 165.8 mg KOH/g |
| Odor: | practically odorless |

EXAMPLE #27 (118-301-A-OP)
(Preparation of Cetearyl Octanoate by Other Process)

In 2000 ml four neck round bottom flask equipped with glass stirrer, distillation head, condenser, thermometer and receiver, added 628.7 grams (2.45 moles) of Cetearyl Alcohol and 371.3 grams (2.57 moles) of Ethylhexanoic Acid. The temperature was raised to 80° C. with good flow of nitrogen. At 80° C. added 3.00 grams of Stannous Oxalate and continued to heat to 200° C. maintaining a good flow of nitrogen over one hour. The reaction mixture was then raised to 220° C. in next hour and held for five hours. The distillate (water of reaction) collected was 43.8 grams against theoretical estimates of 46.4 grams. The ester had the acidity of 6.4 mg KOH/g. The reaction mixture was cooled to 100° C. and added 7.5 grams 35% Hydrogen Peroxide. Mixed the reaction mass at 100° C. for an hour and then cooled to 40° C. To the 930 grams crude ester added pre-dissolved 12.0 grams Sodium Sulfate and 10.0 grams Sodium Carbonate in 200 grams water. Heated the mixture to 80° C. Separation was observed upon standing for an hour with 52 grams of Interphase. The wash procedure repeated two more times with pre-dissolved 12.0 grams Sodium Sulfate in 200 grams of water. In both cases approximately 10 grams of Interphase was found upon standing. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter acids. Mixed the refined eater for 30 minutes and filtered on Buckner Funnel with Whatman Paper #42.

The following physical and chemical properties were observed:

| | |
|---|---|
| Yield: | 821 grams |
| Yield % : | 88.28 |
| Appearance: | Clear liquid |
| Acid Value: | 0.03 mg KOH/g |
| Water %: | 0.01 |
| Color: | <10 APHA |
| Saponification Value: | 141 mg KOH/g |
| Odor: | strong odor |

EXAMPLE #28 (118-301-B-NP)
(Cetearyl Octanoate)

This preparation was of 10,000-lb. batch size using the process of this invention as shown in Example #13.

EXAMPLE #29 (118-310)
(Preparation of $C_{12-15}$ Alkyl Benzoate per U.S. Pat. No. 4,322,545 to Scala)

In 1000 ml four neck round bottom flask equipped with glass stirrer, distillation head, condenser, thermometer and receiver, added 368.1 grams (1.805 moles) of Neodol 25. (Shell Chemical Company), 225.54 grams (1.850 moles) of Benzoic Acid, and 12 grams of Methane Sulfonic Acid. The temperature was raised to 170° C. with good flow of nitrogen in next two hours and held for 4 hours so at 170° C. until acid value <10 mg. KOH/g. The distillate (water of reaction) collected was 30 grams against theoretical estimates of 33.2 grams. The reaction mixture was cooled to 100° C. and added 2 grams of 35% Hydrogen Peroxide. The resulting light colored ester was cooled to 40° C. To the 560 grams crude ester added pre-dissolved 2.8 grams Sodium Chloride and 5.6 grams Sodium Carbonate in 90 grams water. Heated the mixture to 80° C. Separation was observed upon standing for an hour with a big amount of Interphase of approximately 46 grams. The wash procedure was repeated two more times with predissolved 2.85 grams Sodium Chloride in 90 grams of water. The washed aqueous ester was then heated to 120° C. with a vacuum of 30" Hg to remove any residual moisture and organic volatiles. When the moisture was <0.05%, cooled the mass 10 to 40° C. and added 0.1 grams of Diatomaceous Earth filter aids. Mixed the refined ester for 30 minutes and filtered on Buckner Funnel with Whatman Paper #42.

The following physical and chemical properties were observed:

| | |
|---|---|
| Yield: | 500 grams |
| Yield % : | 89.28 |
| Loss During Washing % : | 10.72 |
| Appearance: | Clear liquid |
| Acid Value: | 0.01 mg KOH/g |
| Water % : | 0.02 |
| Refractive Index: | 1.4835 |
| Color: | 70 APHA |
| Saponification Value: | 171.6 mg KOH/g |
| Odor: | Strong odor |

The foregoing Ex. #29 follows Example Nos. 1, 2 and 3 of U.S. Pat. No. 4,322,545 to Scala, except that use of hydrogen peroxide is not taught in the '545 Patent. Hydrogen peroxide has been added in Ex. #29 at 100° C. to demonstrate that addition of hydrogen peroxide yields an ester of strong odor, and yet has higher color, too.

EXAMPLE #30 (118-311)
(Preparation of $C_{12-15}$ Alkyl Benzoate per U.S. Pat. No. 4,322,545 to Scala)

In 1000 ml four neck round bottom flask equipped with glass stirrer, distillation head, condenser, thermometer and receiver, added 368.1 grams (1.805 moles) of Neodol 25 (Shell Chemical Company), 225.54 grams (1.850 moles) of Benzoic Acid, and 12 grams of Methane Sulfonic Acid. The temperature was raised to 170° C. with good flow of nitrogen in next two hours and held for 4 hours at 170° C. until acid value <10 mg. KOH/g. The distillate (water of reaction) collected was 30 grams against theoretical estimates of 33.2 grams. The reaction mixture was cooled to 40° C. To the 560 grams light-yellow colored, crude ester was added pre-dissolved 2.8 grams Sodium Chloride and 5.6 grams Sodium Carbonate in 90 grams water. Heated the mixture to 80° C. Separation was observed upon standing for an hour with a big amount of Interphase of approximately 49 grams. The wash procedure was repeated two more times with predissolved 2.85 grams Sodium Chloride in 90 grams of water. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous-Earth filter aids. Mixed the refined ester for 30 minutes and filtered on Buckner Funnel with Whatman Paper #42.

The following physical and chemical properties were observed:

| Yield: | 498 grams |
|---|---|
| Yield %: | 88.93 |
| Loss During Washing %: | 11.07 |
| Appearance: | Light-yellowish color clear liquid |
| Acid Value: | 0.01 mg KOH/g |
| Water %: | 0.03 |
| Refractive Index: | 1.4835 |
| Color: | 100 APHA |
| Saponification Value: | 171.4 mg KOH/g |
| Odor: | Strong odor |

The foregoing Ex. #30 follows Example Nos. 1, 2 and 3 of U.S. Pat. No. 4,322,545 to Scala. Hydrogen peroxide is not added. The resulting product has even worse color and odor than Ex. #29 above, where hydrogen peroxide was added.

EXAMPLE #31 (118-312)

(Preparation of Octyldodecyl Benzoate as per U.S. Pat. No. 4,791,097 to Walele et al.)

In 1000 ml four neck round bottom flask equipped with glass stirrer, distillation head, condenser, thermometer and receiver, added 426 grams (1.43 moles) of STANDAMUL G from Henkel Co. (Octyldodecanol). Pretreated with 30 mgms of Sodium Borohydride and 172.8 gms (1.41 moles) of Benzoic Acid. The temperature was raised to 80° C. with good flow of Nitrogen. At 80° C., added 0.9 grams of Stannous oxalate and continued to heat to 200° C. maintaining a good flow of nitrogen over 1 hour. The reaction mixture was then raised to 255° C. in next 2 hours and held at 255° C. for one hour. The distillate (water of reaction) collected was 22 grams against theoretical estimates of 25.4 grams. The ester had the acidity of <10 mg. KOH/g. The reaction mixture was cooled to 60° C. To the 575 grams crude ester, added 3.0 grams of Sodium Chloride, 5.43 grams Sodium Carbonate, and 3.0 grams 35% Hydrogen Peroxide predissolved in 90 grams water. Heated the mixture to 80° C. Separation was observed upon standing for an hour with a big amount of Interphase of approximately 60 grams. The wash procedure was repeated two more times with predissolved 3.0 grams Sodium Chloride in 90 grams of water. The washed aqueous ester was then heated to 120° C. with a vacuum of 30" Hg to remove any residual moisture and organic volatiles. When the moisture was <0.05%, cooled the mass to 40° C. and added 0.1 grams of Diatomaceous Earth filter aids. Mixed the refined ester for 30 minutes and filtered on Buckner Funnel with Whatman Paper #42.

The following physical and chemical properties were observed:

| Yield: | 505 grams |
|---|---|
| Yield %: | 87.82 |
| Loss During Washing %: | 12.18 |
| Appearance: | Clear liquid |
| Acid Value: | 0.02 mg KOH/g |
| Water %: | 0.025 |
| Color: | 40 APHA |
| Saponification Value: | 131 mg KOH/g |
| Odor: | Strong odor |

The foregoing Ex. #31 follows Example No. 1 of U.S. Pat. No. 4,791,097 to Walele et al. Hydrogen peroxide is added simultaneously during and at the time of neutralization. The resulting ester has strong odor and high color. In contrast, the invention process uses hydrogen peroxide, if at all, after the neutralization, and not before or at the time of neutralization.

Personal Care Product Formulations Containing Benzoic Acid Esters

To further demonstrate the superiority of the esters of the invention, a series of formulations was prepared comparing the odor characteristics of various personal care products formulated with the compositions of the invention, and with other esters which are commonly used in such types of products. The products specifically included a moisturizing body lotion, an emollient cleansing lotion, and a makeup remover gel. These are considered to be representative of formulations wherein the esters of the invention find application.

Properties of and Uses for Benzoic Acid Ester Compositions

The formulations containing the esters of this invention do not need a higher level of fragrance to mask their presence due to their zero odor or none/negligible odor. Such formulations are desired where unfragranced products are made on demand by consumers. This is also a trend on the market place for hypoallergenic formulations.

EXAMPLE #32

An unfragranced, moisturizing body lotion prepared using the compositions of the present invention has outstanding attributes in that the benzoate esters of this invention, when utilized as a emollient, impart practically no odor of their own to the moisturizing body lotion. Additionally, the body lotion, when applied to the skin, produces a pleasant sensation, and conditions the skin. A representative moisturizing body lotion formulation was prepared, utilizing the following ingredients in the proportions indicated:

TABLE IF

Light Moisturizing Lotion for Table I

| Ingredients (INCI) | % BY WT. |
|---|---|
| A. Water | 85.0 |
| Carbomer (Ultrez 10)[1] | 0.6 |
| Propylene Glycol | 3.0 |
| Sodium C12–15 Pareth-8 Carboxylate (SURFINE WLG-2 CONC.)[2] | 0.3 |
| B. Emollient Ester | 10.0 |
| C. Triethanolamine, 99% | 0.6 |
| D. Propylene Glycol, Diazolidinyl Urea, Methylparaben and Propylparaben (Germaben 11)[3] | 0.5 |

[1]B F Goodrich Company, Cleveland, OH 44131
[2]Finetex, Inc., Elmwood Park, NJ 07407
[3]ISP, Wayne, NJ 07470

Procedure

1. Disperse carbomer in water. Heat to 65° C.–70° C. Add propylene glycol and SURFINE WLG-2 CONC.
2. Weigh (B) items. Heat to 65° C.–70° C.
3. Add (B) to (A) with stirring.
4. Add triethanolamine with vigorous stirring.
5. Cool to 45° C. Add preservative. Continue stirring to room temperature.

EXAMPLE #33

In this Example, another moisturizing body lotion was prepared, fragranced at two levels. The formulation was as follows:

TABLE IIF

Light Moisturizing Lotions for Table II-A and II-B

| Ingredients (INCI) | | % by wt. Fragrance Level A | B |
|---|---|---|---|
| A. | Water | 84.90 | 84.80 |
| | Carbomer (Ultrez 10)[1] | 0.60 | 0.60 |
| | Sodium C12–15 Pareth-8 Carboxylate (SURFINE WLG-2 CONC.)[2] | 0.30 | 0.30 |
| B. | Emollient Ester | 10.00 | 10.00 |
| C. | Triethanolamine, 99% | 0.60 | 0.60 |
| D. | Propylene Glycol, Diazolidinyl Urea, Methylparaben and Propylparaben (Germaben II)[3] | 0.50 | 0.50 |
| | Fragrance Bouquet 39465[4] (1:500 dilute an aliquat in Propylene Glycol) | 0.10 | 0.20 |

[1] B F Goodrich Company, Cleveland, OH 44131
[2] Finetex, Inc., Elmwood Park, NJ 07407
[3] ISP, Wayne, NJ 07470
[4] Intarome Fragrance Corp., Norwood, NJ 07646

Procedure

1. Disperse carbomer in water. Heat to 65° C.–70° C. Add propylene glycol and SURFINE WLG-2 CONC.
2. Weigh (B) items. Heat to 65° C.–70° C.
3. Add (B) to (A) with stirring.
4. Add triethanolamine with vigorous stirring.
5. Cool to 45° C. Add preservative and fragrance. Continue stirring to room temperature.

EXAMPLE #34

An example of a representative emollient cleansing lotion is as follows:

TABLE IV-F

Emollient Cleansing Lotion for Table IV

| Ingredients (INCI) | | % by wt. |
|---|---|---|
| A. | Water | 80.9 |
| | Disodium Oleamide MIPA Sulfosuccinate (FIZUL MD-318C)[1] | 1.0 |
| | Glycerine | 3.0 |
| | Carbomer (Carbopol ETD 2001 Resin)[2] | 0.2 |
| | Tetrasodium EDTA | 0.1 |
| B. | Emollient Ester | 7.5 |
| | Stearic Acid, XXX | 3.0 |
| | Glyceryl Stearate, SE | 2.0 |
| C. | Water | 1.0 |
| | Triethanolamine, 99% | 0.8 |
| D. | Propylene Glycol, Diazolidinyl Urea, Methylparaben and Propylparaben (Germaben II)[3] | 0.5 |

[1] Finetex, Inc. Elmwood Park, NJ 07407
[2] B F Goodrich Company, Cleveland, OH 44131
[3] ISP, Wayne, NJ 07470

Procedure

1. Disperse carbomer into water. Add balance of (A) ingredients and heat to 70° C.–75° C.
2. Mix (B) ingredients together and heat to 70° C.–75° C. Add (B) to (A) with mixing.
3. Combine (C) ingredients, then add to the mixture of (A) & (B).
4. Begin to cool with mixing. At 40° C., add (D). Continue cooling to 30° C. Package in a suitable container.

EXAMPLE #35

An example of make-up remover gel containing an emollient ester is as follows:

TABLE V-F

Make-up Remover Gel for Table V

| Ingredients (INCI) | | % BY WT. |
|---|---|---|
| A. | Emollient Ester | 12.0 |
| | Sodium Laureth-13 carboxylate (SURFINE WLL)[1] | 26.0 |
| | Oleth-2 | 7.0 |
| | Alpha - Tocopherol Acetate | 0.2 |
| | Propylene Glycol | 4.0 |
| | Sorbitol, 70% | 7.0 |
| B. | Water | 43.6 |
| C. | DMDM - Hydantoin | 0.2 |

[1] Finetex Inc. Elmwood Park, NJ 07407

Procedure

Combine components of (A) and mix while heating to 75° C. Heat water to 75° C.–80° C. and add to (A). Continue mixing as it cools. At 55° C., add DMDM—Hydantoin and continue mixing until 45° C. and package in a suitable container.

EXAMPLE #36

Odor Panel Test Results

The odor/fragrance panel tests conducted were subjective in nature—nine individuals were requested to evaluate the odor using a scale of 1 to signify the "least" odor, and 10 for the "most" odor. The results are set forth in Tables I, IIA and IIB, IIIA through IIID, IV and V, from which it will be seen that the esters of this invention are superior in having significantly less odor than esters produced by conventional processes.

The average score is shown to be less than 2 for the esters of this invention versus an average score of greater than 7 for the esters of the other processes. The gap between the two ratings is very extensive, demonstrating the superiority of the esters of this invention in terms of odor.

The importance of this lack of odor is especially critical in fragrance applications, where it is noted that all formulations have a minimum fragrance level (MFL) at which the formulation no longer has an inherent odor. To establish a detectable level of fragrance, a slight increase in fragrance level must be achieved to overcome the inherent odor of the formulation. That is to say, to overcome odors, it is necessary to use more fragrance.

Table I shows the odor panel results for the unfragranced series, namely, on the moisturizing body lotion formulated as in Table I-F (Example #29 above), where no fragrance is added to the formulation. The odor results of the unfragranced series shows the superiority of the esters of the present invention vs. the esters manufactured by prior art processes. The odor of the control formulation (water instead of ester) is 1. The esters of this invention give formulations that are distinctly close in fragrance/odor of the blank control formulation containing water instead of the emollient ester, other ingredients remaining common to all formulations. The formulations AA, BB, CC, and DD containing the esters of the present invention are odorless. The esters of the other processes A, B, C, and D, are easily identified in their respective formulations by their respective typical/characteristic odors.

Tables II-A and II-B show the odor panel results for the fragranced series, namely, on the moisturizing body lotion formulated as in Table II-F (Example #30 above). The fragranced series of tests was conducted to demonstrate that the esters of the invention allow the reduced use of fragrance as compared to the conventional esters of other processes.

Referring to Tables II-A and II-B, the fragranced formulations series, the fragrance used was at two levels: level A was at 0.10% and level B was at 0.20%. In this series, each ester of the invention and the equivalent esters of the other process were compared at both levels of fragrance.

The esters of this invention show that a lower level of fragrance is adequate to produce a perfumed product. The products of the other process need higher levels of fragrance to produce an equal strength perfumed product. This also indicates that any odor-masking requirement of the esters produced by other processes consumed or demanded a higher level dose of fragrance in over-coming their respective characteristic odors. This further indicates that the MFL (Minimum Fragrance Level) for esters of this invention is lower than the MFL of esters of the other processes. The fragrance of the formulations containing esters of this invention showed lower ratings, thus demonstrating superiority to the esters of other processes at both levels of fragrance.

The same phenomenon is expected in other personal care product formulations which advantageously use esters of this invention.

The results of odor or perfume/fragrance reduction panel tests are shown in Tables I, II-A and II-B for cosmetics/personal care formulations described above in Examples # 29-32. By the Odor AS IS Basis is meant odor panel comparisons done on the neat (as is) products of this invention vs. the products of the other processes.

EXAMPLE 37

Results of Odor Panel Tests for FINESOLV TN, FINESTER EH-25, FINESTER CST-8, and FINSOLV PG-22.

A further evaluation of odor was conducted for compositions in accordance with the invention, and for esters produced in accordance with known processes. More specifically, esters described in the above Examples, produced in accordance with the process of the invention and by known processes, were compared by again requesting 9 individuals to evaluate odor using a scale of 1 to equal "least" and 10 to equal "most". The results are set forth in Tables III-A through III-D, from which it is clear that the esters of the invention are far superior to products including FINESOLV TN, FINESTER EH-25, FINESTER CST-8, and FINSOLV PG-22.

TABLE III compares odor, color and yields for each of the ester prepared in Examples 1 through 17, 25–27, and 29–30. It will be seen that esters prepared by the process of the invention are superior in odor, color and yield to esters prepared by known processes.

In conclusion, the esters of the invention are surprisingly found to be virtually lacking in detectable odor, superior in color, and produced in greater yields.

It will be understood that the embodiments described herein are merely exemplary and that a person skilled in the art may make many variations and modifications without departing from the spirit and scope of the invention. For example, the invention is not intended to be strictly limited to the named reactants and catalysts, recited pH ranges, reaction temperatures, reaction conversion, or other parameters. Rather, the invention as claimed extends to many possible variations not specifically detailed. All such variations and modifications are intended to be included in the scope of the invention as described herein.

TABLE I

Odor Panel Results on Moisturizing Body Lotion (Unfragranced Series)
See Formulation Table I-F

|  |  | A | B | C | D | AA | BB | CC | DD |
|---|---|---|---|---|---|---|---|---|---|
|  |  | \multicolumn{4}{c}{Other Process} | \multicolumn{4}{c}{New Invention Process} |
|  | Control | C12–15 Alkyl Benzoate | Dipropylene Glycol Dibenzoate | C12–15 Alkyl Octanoate | Cetearyl Octanoate | C12–15 Alkyl Benzoate | Dipropylene Glycol Dibenzoate | C12–15 Alkyl Octanoate | Cetearyl Octanoate |
| Emollient Esters of: |  |  |  |  |  |  |  |  |  |
| Other Process | None | + | + | + | + | — | — | — | — |
| New Process | None | — | — | — | — | + | + | + | + |
| Example # | Water | 4 | 16 | 14 | 12 | 6 | 17 | 15 | 13 |
| Odor Panel Results |  |  |  |  |  |  |  |  |  |

1 = Best
10 = Worst

TABLE I-continued

Odor Panel Results on Moisturizing Body Lotion (Unfragranced Series)
See Formulation Table I-F

|  | A | B | C | D | AA | BB | CC | DD |
|---|---|---|---|---|---|---|---|---|
|  |  | Other Process | | | New Invention Process | | | |
|  | Control | C12–15 Alkyl Benzoate | Dipropylene Glycol Dibenzoate | C12–15 Alkyl Octanoate | Cetearyl Octanoate | C12–15 Alkyl Benzoate | Dipropylene Glycol Dibenzoate | C12–15 Alkyl Octanoate | Cetearyl Octanoate |

Panel Ratings:

|  | A | B | C | D | AA | BB | CC | DD |
|---|---|---|---|---|---|---|---|---|
| 1. | 1 | 8 | 9 | 9 | 8 | 2 | 2 | 2 | 2 |
| 2. | 1 | 9 | 7 | 10 | 8 | 3 | 2 | 1 | 2 |
| 3. | 1 | 10 | 8 | 8 | 9 | 2 | 1 | 3 | 1 |
| 4. | 1 | 7 | 8 | 9 | 8 | 3 | 2 | 1 | 2 |
| 5. | 1 | 7 | 7 | 8 | 10 | 1 | 1 | 2 | 1 |
| 6. | 1 | 8 | 7 | 7 | 8 | 2 | 1 | 1 | 3 |
| 7. | 1 | 9 | 8 | 9 | 9 | 1 | 1 | 2 | 2 |
| 8. | 1 | 8 | 8 | 8 | 8 | 1 | 1 | 1 | 1 |
| 9. | 1 | 7 | 9 | 8 | 10 | 2 | 2 | 1 | 2 |
| Total Score = | 9.0 | 73 | 71 | 76 | 78 | 17 | 13 | 14 | 16 |
| Average Score = | 1.00 | 8.11 | 7.88 | 8.44 | 8.66 | 1.88 | 1.44 | 1.55 | 1.77 |

TABLE II-A

Odor Panel Results on Moisturizing Body Lotion
(fragranced Series: Level A @ 0.10% of Fragance)
See Formulation Table II-F

|  | A | B | C | D | AA | BB | CC | DD |
|---|---|---|---|---|---|---|---|---|
|  |  | Other Process | | | New Invention Process | | | |
|  | Control | C12–15 Alkyl Benzoate | Dipropylene Glycol Dibenzoate | C12–15 Alkyl Octanoate | Cetearyl Octanoate | C12–15 Alkyl Benzoate | Dipropylene Glycol Dibenzoate | C12–15 Alkyl Octanoate | Cetearyl Octanoate |

Emollient Esters of:

|  |  | A | B | C | D | AA | BB | CC | DD |
|---|---|---|---|---|---|---|---|---|---|
| Other Process | None | + | + | + | + | — | — | — | — |
| New Process | None | — | — | — | — | + | + | + | + |
| Example # | Water | 4 | 16 | 14 | 12 | 6 | 17 | 15 | 13 |

Odor Panel Results

1 = Best
10 = Worst
Panel Ratings:

|  | A | B | C | D | AA | BB | CC | DD |
|---|---|---|---|---|---|---|---|---|
| 1. | 1 | 7 | 8 | 8 | 7 | 2 | 2 | 2 | 1 |
| 2. | 1 | 7 | 7 | 8 | 7 | 1 | 2 | 1 | 2 |
| 3. | 1 | 7 | 8 | 9 | 8 | 1 | 1 | 1 | 1 |
| 4. | 1 | 8 | 8 | 8 | 9 | 2 | 1 | 1 | 1 |
| 5. | 1 | 8 | 7 | 7 | 7 | 1 | 2 | 2 | 2 |
| 6. | 1 | 7 | 6 | 8 | 8 | 1 | 1 | 1 | 1 |
| 7. | 1 | 6 | 6 | 8 | 7 | 1 | 1 | 1 | 2 |
| 8. | 1 | 7 | 7 | 7 | 9 | 1 | 2 | 2 | 1 |
| 9. | 1 | 8 | 7 | 9 | 8 | 1 | 2 | 1 | 1 |
| Total Score = | 9 | 65 | 64 | 72 | 70 | 11 | 14 | 12 | 12 |
| Average Score = | 1.0 | 7.22 | 7.11 | 8.00 | 7.77 | 1.22 | 1.55 | 1.33 | 1.33 |

TABLE II-B

Odor Panel Results on Moisturizing Body Lotion
(Fragranced Series: Level B @ 0.2% of Fragance)
See Formulation Table II-F

|  | Control | A | B | C | D | AA | BB | CC | DD |
|---|---|---|---|---|---|---|---|---|---|
|  |  | Other Process | | | | New Invention Process | | | |
|  |  | C12–15 Alkyl Benzoate | Dipropylene Glycol Dibenzoate | C12–15 Alkyl Octanoate | Cetearyl Octanoate | C12–15 Alkyl Benzoate | Dipropylene Glycol Dibenzoate | C12–15 Alkyl Octanoate | Cetearyl Octanoate |
| Emollient Esters of: | | | | | | | | | |
| Other Process | None | + | + | + | + | — | — | — | — |
| New Process | None | — | — | — | — | + | + | + | + |
| Example # | Water | 4 | 16 | 14 | 12 | 6 | 17 | 15 | 13 |
| Odor Panel Results | | | | | | | | | |
| 1 = Best | | | | | | | | | |
| 10 = Worst | | | | | | | | | |
| Panel Ratings: | | | | | | | | | |
| 1. | | 1 | 6 | 7 | 7 | 6 | 1 | 2 | 1 | 1 |
| 2. | | 1 | 7 | 6 | 7 | 6 | 2 | 1 | 1 | 2 |
| 3. | | 1 | 6 | 7 | 8 | 7 | 1 | 1 | 2 | 1 |
| 4. | | 1 | 6 | 7 | 7 | 8 | 1 | 1 | 1 | 1 |
| 5. | | 1 | 5 | 6 | 6 | 6 | 2 | 2 | 1 | 1 |
| 6. | | 1 | 5 | 6 | 7 | 7 | 1 | 1 | 1 | 2 |
| 7. | | 1 | 6 | 7 | 7 | 7 | 1 | 1 | 1 | 1 |
| 8. | | 1 | 6 | 7 | 8 | 8 | 1 | 2 | 2 | 1 |
| 9. | | 1 | 6 | 7 | 7 | 7 | 1 | 1 | 1 | 1 |
| Total Score = | | 9 | 53 | 54 | 64 | 62 | 11 | 12 | 11 | 11 |
| Average Score = | | 1.0 | 5.88 | 6.0 | 7.11 | 6.88 | 1.22 | 1.33 | 1.22 | 1.22 |

TABLE III

Comparison Of Odor, Color, and % Yield

| Process[1] | Example # | Odor | APHA[2] Color | % Yields |
|---|---|---|---|---|
| NP | 1. (115-178) | Odorless | 15 | 97.75 |
| OP | 2. (112-51) | Strong Odor | 5 | 95.00 |
| NP | 3. (121-90) | Odorless | 20 | 96.25 |
| OP | 4. (112-141) | Mild Odor | 5 | 96.00 |
| OP | 5. (Motherbatch) (115-72) | Odorless | 20 | 93.33 |
| OP | 6. (115-174) | Strong Odor | 10 | 91.66 |
|  | 7. (115-176) | Odorless | 20 | 95.00 |
|  | 8. (118-76) | Mild Odor | 5 | 94.41 |
| NP | 9. (118-78) | Mild Odor | 5 | 98.53 |
| NP | 10. (118-89) | Odorless | 5 | 97.05 |
| NP | 11. (118-92) | Mild Odor | 5 | 95.58 |
| OP | 12. (115-169) | Strong Odor | 10 | 86.66 |
| NP | 13. (118-245) | Odorless | 20 | 98.00 |
| OP | 14. (95-131) | Strong Odor | 10 | 92.00 |
| NP | 15. (118-221) | Odorless | 10 | 96.66 |
| OP | 16. (105-138) | Strong Odor | 10 | 83.33 |
| NP | 17. (118-137) | Odorless | 10 | 93.20 |
| NP | 25. (118-225) | Odorless | 10 | 88.33 |
| NP | 26. (118-227) | Odorless | 20 | 91.66 |
| OP | 27. (118-301A) | Strong Odor | 10 | 88.28 |
| OP | 29. (118-310) | Strong Odor | 70 | 89.28 |
| OP | 30. (118-311) | Strong Odor | 100 | 88.93 |
| OP | 31. (118-312) | Strong Odor | 40 | 87.82 |

[1]NP = New Process, OP = Other Process
[2]APHA SCALE = American Public Health Association ASTM D-1209

TABLE III-A

Odor Panel Results on C12–15 Alkyl Benzoate (FINSOLV TN)[1]
Other Process vs. Invention Process

| Panel | 1 | 2 | 3 | 4 | 5 | 6 | 7 | 8 | 9 |
|---|---|---|---|---|---|---|---|---|---|
| Old Process Series | | | | | | | | | |
| Example #18 Lot A (Ref. #118-288-A) | 9 | 9 | 5 | 10 | 9 | 9 | 9 | 10 | 10 |
| Example #19 | 7 | 9 | 8 | 10 | 10 | 10 | 4 | 9 | 10 |

TABLE III-A-continued

Odor Panel Results on C12–15 Alkyl Benzoate (FINSOLV TN)[1]
Other Process vs. Invention Process

| Panel | 1 | 2 | 3 | 4 | 5 | 6 | 7 | 8 | 9 |
|---|---|---|---|---|---|---|---|---|---|
| Lot B (Ref. #118-288-B) Example #2 | 10 | 8 | 10 | 9 | 10 | 9 | 8 | 8 | 7 |
| Lot C (Ref. #112-51) Example #20 | 6 | 7 | 4 | 6 | 10 | 5 | 5 | 4 | 5 |
| Lot D (Ref. #118-288-D) Example #4 | 6 | 6 | 9 | 6 | 8 | 7 | 7 | 3 | 5 |
| Lot E (Ref. #112-141) Example #21 | 6 | 6 | 7 | 7 | 9 | 6 | 6 | 4 | 5 |
| Lot F (Ref. #118-288-F) | | | | | | | | | |
| New Process Series | | | | | | | | | |
| Example #22 | 1 | 1 | 4 | 2 | 2 | 1 | 4 | 2 | 1 |
| Lot A (Ref. #118-288-A-NP) Example #6 | 1 | 1 | 2 | 1 | 1 | 1 | 3 | 2 | 1 |
| Lot B (Ref. #115-174) Example #22-C | 2 | 1 | 3 | 2 | 2 | 1 | 2 | 1 | 1 |
| Lot C (Ref. #118-288-C-NP) Example #1 | 1 | 2 | 2 | 1 | 1 | 2 | 1 | 1 | 1 |
| Lot D (Ref. #115-178) | | | | | | | | | |
| Rating: | 10 Worst | | | | | | | | |
| | 1 Best | | | | | | | | |
| Results: | | | | | | | | | |
| Average of Panelists and Products | Other Process | 7.30 | | | | | | | |
| | New Process | 1.70 | | | | | | | |

[1]Finetex, Inc., Elmwood Park, NJ 07407

TABLE III-B

Odor Panel Results on C12–15 Alkyl Octanoate (FINESTER EH-25)[1]
Other Process vs. New Invention Process

| Panel | 1 | 2 | 3 | 4 | 5 | 6 | 7 | 8 | 9 |
|---|---|---|---|---|---|---|---|---|---|
| Old Process Series | | | | | | | | | |
| Example #14 | 8 | 9 | 8 | 8 | 10 | 7 | 8 | 8 | 8 |
| Lot A (Ref. #118-300-A) Example #23 | 8 | 10 | 6 | 9 | 8 | 8 | 7 | 9 | 7 |
| Lot B (Ref. #118-300-B) Example #24 | 9 | 8 | 7 | 7 | 7 | 7 | 9 | 8 | 9 |
| Lot C (Ref. #118-300-C) | | | | | | | | | |
| New Process Series | | | | | | | | | |
| Example #15 | 2 | 1 | 1 | 2 | 2 | 2 | 2 | 2 | 1 |
| Lot A (Ref. 118-221) Example #25 | 2 | 2 | 3 | 1 | 1 | 2 | 1 | 1 | 1 |
| Lot B (Ref. #118-225) Example #26 | 2 | 1 | 1 | 1 | 2 | 2 | 1 | 2 | 2 |
| Lot C (Ref. #118-227) | | | | | | | | | |
| Rating: | 10 Worst | | | | | | | | |
| | 1 Best | | | | | | | | |
| Results: | | | | | | | | | |
| Average of Panelists and Products | Other Process | 8.03 | | | | | | | |
| | New Process | 1.59 | | | | | | | |

[1]Finetex, Inc., Elmwood Park, NJ 07407

TABLE III-C

Odor Panel Results on C12–15 Cetearyl Octanoate (FINESTER CST-8)[1]
Other Process vs. New Invention Process

| Panel | 1 | 2 | 3 | 4 | 5 | 6 | 7 | 8 | 9 |
|---|---|---|---|---|---|---|---|---|---|
| Old Process Series | | | | | | | | | |
| Example #12 | 8 | 9 | 10 | 9 | 10 | 9 | 8 | 10 | 8 |
| Lot A (Ref. #115-169) | | | | | | | | | |

TABLE III-C-continued

Odor Panel Results on C12–15 Cetearyl Octanoate (FINESTER CST-8)[1]
Other Process vs. New Invention Process

| Panel | 1 | 2 | 3 | 4 | 5 | 6 | 7 | 8 | 9 |
|---|---|---|---|---|---|---|---|---|---|
| Example #27 Lot B (Ref. #118-301) | 10 | 10 | 8 | 8 | 7 | 7 | 10 | 8 | 9 |
| New Process Series | | | | | | | | | |
| Example #13 Lot. A (Ref. #118-245) | 1 | 2 | 3 | 2 | 1 | 3 | 2 | 1 | 2 |
| Example #28 Lot B (Ref. #118-301-B) | 2 | 2 | 1 | 1 | 3 | 1 | 2 | 2 | 1 |
| Rating: | 10 Worst | | | | | | | | |
| | 1 Best | | | | | | | | |
| Results: | | | | | | | | | |
| Average of Panelists and Products | Other Process | 7.78 | | | | | | | |
| | New Process | 1.77 | | | | | | | |

[1]Finetex, Inc., Elmwood Park, NJ 07407

TABLE III-D

Odor Panel Results on Dipropylene Glycol Dibenzoate (FINSOLV PG-22)[1]
Other Process vs. New Invention Process

| Panel | 1 | 2 | 3 | 4 | 5 | 6 | 7 | 8 | 9 |
|---|---|---|---|---|---|---|---|---|---|
| Old Process | | | | | | | | | |
| Example #16 (Ref. #105-138) | 9 | 8 | 10 | 10 | 7 | 8 | 9 | 8 | 8 |
| New Process | | | | | | | | | |
| Example #17 (Ref. #118-137) | 2 | 1 | 2 | 1 | 2 | 3 | 1 | 3 | 2 |
| Rating: | 10 Worst | | | | | | | | |
| | 1 Best | | | | | | | | |
| Results: | | | | | | | | | |
| Average of Panelists and Products | Other Process | 7.56 | | | | | | | |
| | New Process | 1.89 | | | | | | | |

[1]Finetex, Inc., Elmwood Park, NJ 07407

TABLE IV

Odor Panel Results on Emollient Cleansing Lotion
See Formulation Table III

| | | A | B | C | D | AA | BB | CC | DD |
|---|---|---|---|---|---|---|---|---|---|
| | | | Other Process | | | | New Invention Process | | |
| | Control | C12–15 Alkyl Benzoate | Dipropylene Glycol Dibenzoate | C12–15 Alkyl Octanoate | Cetearyl Octanoate | C12–15 Alkyl Benzoate | Dipropylene Glycol Dibenzoate | C12–15 Alkyl Octanoate | Cetearyl Octanoate |
| Emollient Esters of: | | | | | | | | | |
| Other Process | None | + | + | + | + | — | — | — | — |
| New Process | None | — | — | — | — | + | + | + | + |
| Example # | Water | 4 | 16 | 14 | 12 | 6 | 17 | 15 | 13 |
| Odor Panel Results | | | | | | | | | |

1 = Best
10 = Worst
Panel Ratings:

| | | | | | | | | | |
|---|---|---|---|---|---|---|---|---|---|
| 1. | 1 | 9 | 8 | 8 | 10 | 3 | 2 | 4 | 4 |
| 2. | 1 | 10 | 9 | 9 | 9 | 4 | 2 | 3 | 4 |
| 3. | 1 | 9 | 10 | 8 | 9 | 2 | 4 | 3 | 3 |
| 4. | 1 | 8 | 9 | 9 | 10 | 3 | 4 | 2 | 3 |
| 5. | 1 | 9 | 8 | 10 | 8 | 4 | 3 | 4 | 4 |
| 6. | 1 | 8 | 8 | 9 | 9 | 3 | 2 | 4 | 2 |

TABLE IV-continued

Odor Panel Results on Emollient Cleansing Lotion
See Formulation Table III

| | | A | B | C | D | AA | BB | CC | DD |
|---|---|---|---|---|---|---|---|---|---|
| | | | Other Process | | | | New Invention Process | | |
| | Control | C12–15 Alkyl Benzoate | Dipropylene Glycol Dibenzoate | C12–15 Alkyl Octanoate | Cetearyl Octanoate | C12–15 Alkyl Benzoate | Dipropylene Glycol Dibenzoate | C12–15 Alkyl Octanoate | Cetearyl Octanoate |
| 7. | 1 | 8 | 9 | 9 | 10 | 4 | 3 | 2 | 3 |
| 8. | 1 | 9 | 8 | 9 | 9 | 2 | 4 | 3 | 2 |
| 9. | 1 | 8 | 10 | 9 | 10 | 2 | 4 | 3 | 4 |
| Total Score = | 9 | 78 | 79 | 80 | 84 | 27 | 30 | 28 | 29 |
| Average Score = | 1.0 | 8.66 | 8.77 | 8.88 | 9.33 | 3.0 | 3.33 | 3.11 | 3.22 |

TABLE V

Odor Panel Results on Make-up Remover Gel
See Formulation Table V-F

| | | A | B | C | D | AA | BB | CC | DD |
|---|---|---|---|---|---|---|---|---|---|
| | | | Other Process | | | | New Invention Process | | |
| | Control | C12–15 Alkyl Benzoate | Dipropylene Glycol Dibenzoate | C12–15 Alkyl Octanoate | Cetearyl Octanoate | C12–15 Alkyl Benzoate | Dipropylene Glycol Dibenzoate | C12–15 Alkyl Octanoate | Cetearyl Octanoate |
| Emollient Esters of: | | | | | | | | | |
| Other Process | None | + | + | + | + | — | — | — | — |
| New Process | None | — | — | — | — | + | + | + | + |
| Example # | Water | 4 | 16 | 14 | 12 | 6 | 17 | 15 | 13 |
| Odor Panel Results | | | | | | | | | |
| 1 = Best | | | | | | | | | |
| 10 = Worst | | | | | | | | | |
| Panel Ratings: | | | | | | | | | |
| 1. | 1 | 8 | 9 | 8 | 9 | 2 | 2 | 3 | 3 |
| 2. | 1 | 9 | 8 | 9 | 8 | 3 | 4 | 2 | 3 |
| 3. | 1 | 8 | 9 | 8 | 9 | 1 | 3 | 3 | 3 |
| 4. | 1 | 10 | 9 | 9 | 8 | 1 | 2 | 2 | 2 |
| 5. | 1 | 9 | 8 | 10 | 8 | 2 | 2 | 2 | 3 |
| 6. | 1 | 8 | 9 | 9 | 9 | 1 | 2 | 2 | 2 |
| 7. | 1 | 8 | 8 | 8 | 9 | 3 | 3 | 2 | 2 |
| 8. | 1 | 9 | 8 | 8 | 8 | 1 | 2 | 2 | 2 |
| 9. | 1 | 8 | 8 | 9 | 9 | 1 | 2 | 3 | 2 |
| Total Score = | 9 | 82 | 76 | 78 | 77 | 15 | 19 | 21 | 22 |
| Average Score = | 1.0 | 9.11 | 8.44 | 8.66 | 8.55 | 1.66 | 2.11 | 2.33 | 2.44 |

We claim:

1. A method of reducing or eliminating odor in an ester composition comprising a crude ester and an esterification catalyst comprising the step of removing said catalyst from the crude ester and then adding alkali to neutralize acidity.

2. In a process for preparing odorless, colorless esters from an esterification reaction mixture obtained by reacting an acid and an alcohol in the presence of an effective amount of a catalyst, which comprises adding alkali to the esterification reaction mixture and washing the ester, the improvement which comprises removing said catalyst from said reaction mixture prior to addition of alkali and which further comprises contacting the wet, crude ester with a bleaching agent, after neutralization with said alkali is completed.

3. The process of claim 2 wherein said odorless esters are benzoate esters, octanoate esters, aliphatic emollient esters, or glycol dibenzoate esters, wherein said acid is selected from the group consisting of benzoic acid, ethylhexanoic acid, and linear or branched carboxylic acids with 4 to 22 carbon atoms, and wherein said alcohol has from 3 to 22 carbon atoms.

4. In a process for preparing reduced-odor benzoate esters from an esterification reaction mixture obtained by reacting benzoic acid with an alcohol in the presence of an effective amount of a catalyst, which comprises the steps of:
   heating said reaction mixture;
   collecting distillate comprising the water of reaction;
   neutralizing and washing the acidity of said reaction mixture with at least one alkali;
   drying said ester; and
   filtering the refined ester product;
   the improvement comprising removing said catalyst from said reaction mixture after the reaction is complete, and before neutralization.

5. The process of claim 5 wherein said catalyst comprises an organometallic compound or metal oxide compound.

6. The process of claim 4 wherein said catalyst is stannous oxalate or zinc oxide.

7. The process of claim 4 wherein said catalyst is removed by filtration.

8. The process of claim 4 wherein said neutralization step, the filtered, crude ester is neutral washed with amounts of alkali at least stoichiometric to the acidity of the crude ester.

9. The process of claim 4 wherein said alkali comprises an alkali metal carbonate or alkali metal hydroxide.

10. In a process for preparing reduced-odor benzoate esters from an esterification reaction mixture obtained by reacting benzoic acid with an alcohol in the presence of an effective amount of a catalyst, which comprises the steps of:
heating said reaction mixture;
collecting distillate comprising the water of reaction;
neutralizing and washing the acidity of said reaction mixture with at least one alkali;
drying said ester; and
filtering the refined ester product;
the improvement comprising removing said catalyst from said reaction mixture after the reaction is complete, and before neutralization, and wherein after said neutralization is completed, contacting the wet, crude ester with a bleaching agent.

11. The process of claim 4 wherein said bleaching agent is hydrogen peroxide.

12. In a process for preparing reduced-odor benzoate esters from an esterification reaction mixture obtained by reacting benzoic acid with an alcohol in the presence of an effective amount of a catalyst, which comprises the steps of:
beating said reaction mixture;
collecting distillate comprising the water of reaction;
neutralizing and washing the acidity of said reaction mixture with at least one alkali;
drying said ester; and
filtering the refined ester product;
the improvement comprising removing said catalyst from said reaction mixture after the reaction is complete, and before neutralization, and wherein said wet, crude ester is contacted with a bleaching agent in a first or subsequent washing step, after neutralization is complete.

13. The process of claim 4 wherein said alcohol comprises from 3 to 22 carbon atoms.

14. The process of claim 4 wherein said alcohol comprises 12 to 15 carbon atoms.

15. The process of claim 4 wherein said crude ester has an acidity of no more than 10 mg KOH/g.

16. The process of claim 4 further comprising pretreating said alcohol with sodium borohydride before reacting with benzoic acid and before contacting with said catalyst.

17. The process of claim 4 wherein said neutralization wash further comprises at least one salt selected from the group consisting of sodium chloride, sodium sulfite, potassium chloride and potassium sulfate.

18. The process of claim 4 further comprising the step of cooling said reaction mixture after said reaction is substantially complete and before said neutralization step.

19. The process of claim 4 comprising the step of further washing the resulting crude ester after said neutralization and washing step.

20. The process of claim 19 wherein at least one salt selected from the group consisting of sodium chloride, sodium sulfate, potassium chloride, and potassium sulfate is added in at least one of said washing steps.

21. The process of claim 4 wherein distillate is collected until esterification is substantially complete.

22. The process of claim 4 wherein said process is a batch process.

23. The process of claim 4 wherein said process is a continuous process.

24. The process of claim 23 wherein said process is conducted in a continuous extractor.

25. In a process for preparing reduced-odor octanoate esters from an esterification reaction mixture obtained by reacting ethylhexanoic acid with an alcohol in the presence of an effective amount of a catalyst, which comprises the steps of:
heating said reaction mixture;
collecting distillate comprising the water of reaction;
neutralizing and washing the acidity of said reaction mixture with at least one alkali;
drying said ester; and filtering the refined ester product;
the improvement comprising removing said catalyst from said reaction mixture after the reaction is complete, and before neutralization.

26. The process of claim 25 wherein said alcohol comprises from 3 to 22 carbon atoms.

27. The process of claim 25 wherein said alcohol comprises 12 to 15 carbon atoms.

28. The process of claim 25 wherein said catalyst is stannous oxalate or zinc oxide.

29. In a process for preparing reduced-odor octanoate esters from an esterification reaction mixture obtained by reacting ethylhexanoic acid with an alcohol in the presence of an effective amount of a catalyst, which comprises the steps of:
heating said reaction mixture;
collecting distillate comprising the water of reaction;
neutralizing and washing the acidity of said reaction mixture with at least one alkali;
drying said ester; and
filtering the refined ester product;
the improvement comprising removing said catalyst from said reaction mixture after the reaction is complete, and before neutralization, and wherein after said neutralization is completed, contacting the wet, crude ester with a bleaching agent.

30. In a process for preparing reduced odor aliphatic, emollient esters from an esterification reaction mixture obtained by reacting a carboxylic acid with an alcohol in the presence of an effective amount of a catalyst, which comprises the steps of:
heating said reaction mixture;
collecting distillate comprising the water of reaction;
neutralizing and washing the acidity of said reaction mixture with at least one alkali;
drying said ester; and
filtering the refined ester product;
the improvement comprising removing said catalyst from said reaction mixture after the reaction is complete, and before neutralization.

31. The process of claim 30 wherein said alcohol comprises from 3 to 22 carbon atoms and wherein said carboxylic acid comprises linear or branched carboxylic acids with 4 to 22 carbon atoms.

32. The process of claim 30 wherein said alcohol comprises 12 to 15 carbon atoms.

33. The process of claim 30 wherein said catalyst is stannous oxalate or zinc oxide.

34. In a process for preparing reduced odor aliphatic, emollient esters from an esterification reaction mixture obtained by reacting a carboxylic acid with an alcohol in the presence of an effective amount of a catalyst, wherein said alcohol comprises from 3 to 22 carbon atoms and wherein said carboxylic acid comprises linear or branched carboxylic acids with 4 to 22 carbon atoms, which comprises the steps of:

heating said reaction mixture;

collecting distillate comprising the water of reaction;

neutralizing and washing the acidity of said reaction mixture with at least one alkali;

drying said ester; and filtering the refined ester product;

the improvement comprising removing said catalyst from said reaction mixture after the reaction is complete, and before neutralization, and wherein after said neutralization is completed, contacting the wet, crude ester with a bleaching agent.

35. In a process for preparing reduced odor glycol dibenozate ester from an esterification reaction mixture obtained by reacting a glycol with benzoic acid in the presence of an effective amount of a catalyst, which comprises the steps of:

heating said reaction mixture;

collecting distillate comprising the water of reaction;

neutralizing and washing the acidity of said reaction mixture with at least one alkali;

drying said ester; and filtering the refined ester product;

the improvement comprising removing said catalyst from said reaction mixture after the reaction is complete, and before neutralization.

36. The process of claim 35 wherein said glycol comprises from 3 to 12 carbon atoms.

37. The process of claim 35 wherein said glycol comprises 6 to 12 carbon atoms.

38. The process of claim 35 wherein said glycol is dipropylene glycol.

39. The process of claim 35 wherein said catalyst is stannous oxalate or zinc oxide.

40. In a process for preparing reduced odor glycol dibenozate esters from an esterification reaction mixture obtained by reacting a glycol with benzoic acid in the presence of an effective amount of a catalyst, which comprises the steps of:

heating said reaction mixture;

collecting distillate comprising the water of reaction;

neutralizing and washing the acidity of said reaction mixture with at least one alkali;

drying said ester; and filtering the refined ester product;

the improvement comprising removing said catalyst from said reaction mixture after the reaction is complete, and before neutralization, and wherein after said neutralization is completed, contacting the wet, crude ester with a bleaching agent.

41. The process of claim 4 wherein said alcohol is Neodol 25.

42. The process of claim 25 wherein said alcohol is Neodol 25.

43. The process of claim 30 wherein said alcohol is Neodol 25.

* * * * *